US009493480B2

(12) United States Patent
Posner et al.

(10) Patent No.: US 9,493,480 B2
(45) Date of Patent: *Nov. 15, 2016

(54) MONOMERIC TRIOXANE AMIDE SULFUR COMPOUNDS

(75) Inventors: Gary H. Posner, Baltimore, MD (US); Rachel D. Slack, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 20 days.

This patent is subject to a terminal disclaimer.

(21) Appl. No.: 14/111,991

(22) PCT Filed: Apr. 16, 2012

(86) PCT No.: PCT/US2012/033774
§ 371 (c)(1),
(2), (4) Date: Jul. 25, 2014

(87) PCT Pub. No.: WO2012/142575
PCT Pub. Date: Oct. 18, 2012

(65) Prior Publication Data
US 2015/0183798 A1    Jul. 2, 2015

Related U.S. Application Data

(60) Provisional application No. 61/475,758, filed on Apr. 15, 2011.

(51) Int. Cl.
| | | |
|---|---|---|
| *C07D 493/18* | (2006.01) | |
| *A61K 45/06* | (2006.01) | |
| *A61K 31/357* | (2006.01) | |
| *C07D 493/08* | (2006.01) | |
| *A61K 31/537* | (2006.01) | |

(52) U.S. Cl.
CPC ........... *C07D 493/18* (2013.01); *A61K 31/357* (2013.01); *A61K 31/537* (2013.01); *A61K 45/06* (2013.01); *C07D 493/08* (2013.01)

(58) Field of Classification Search
USPC .......................................... 514/450; 549/348
See application file for complete search history.

(56) References Cited

U.S. PATENT DOCUMENTS 8,884,032 B2 * 11/2014 Posner ................. C07D 493/18
549/348
2009/0291923 A1    11/2009 Posner et al.
2010/0093651 A1    4/2010  Brando et al.

FOREIGN PATENT DOCUMENTS

WO          2010135427 A2    11/2010

OTHER PUBLICATIONS

Vu et al., Synthesis of novel 10-deoxoartemisinins, Advances in Natural Sciences (Hanoi, Viet Nam), 2008, 9(2), 197-201.*
Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Woodard et al., "Malaria-infected mice live until at least day 30 after a new monomeric trioxane combined with mefloquine are administered together in a single low oral dose", Journal of Medicinal Chemistry, 2009, vol. 52, pp. 7458-7462.
Barton et al., "Rationale design of biotinylated antimalarial endoperoxide carbon centered radical prodrugs for applications in proteomics", Journal of Medicinal Chemistry, 2010, vol. 53, pp. 4555-4559.
PCT International Search Report dated Dec. 27, 2012 for corresponding PCT International Patent Application No. PCT/US2012/033774.
Olliaro, P. L.; Boland, P. B. Clinical public health implications of antimalarial drug resistance. In Antimalarial Chemotherapy: Mechanisms of Action, Resistance, and New Directions in Drug Discovery; Rosenthal, P. J., Ed.; Humana Press: Totowa, NJ, 2001; pp. 65-83.
Guidelines for the Treatment of Malaria; World Health Organization: Geneva, 2006.
Ashley, E. A.; White, N. J. Artemisinin-based Combinations. Curr. Opin. Infect. Dis. 2005, 18, 531-536.
Adjuik, M.; Babiker, A.; Garner, P.; Olliaro, P.; Taylor, W.; White, N. Artesunate Combinations for Treatment of Malaria: Meta-analysis. Lancet 2004, 363, 9-17.
Guthmann, J.-P.; Cohuet, S.; Rigutto, C.; Fortes, F.; Saraiva, N.; Kiguli, J.; Kyomuhendo, J.; Francis, M.; Noel, F.; Mulemba, M. Balkan, S. High Efficacy of Two Artemisinin-based Combinations (Artesunate plus Amodiaquine and Artemether plus Lumefantrine) in Caala, Central Angola. Am. J. Trop. Med. Hyg. 2006, 75, 143-145.
Myint, H. Y.; Ashley, E. A.; Day, N. P. J.; Nosten, F.; White, N. J. Efficacy and Safety of Dihydroartemisinin-piperaquine. Trans. R. Soc. Trop. Med. Hyg. 2007, 101, 858-866.
Sirima, S. B.; Tiono, A. B.; Gansane, A.; Diarra, A.; Ouedraogo, A.; Konate, A. T.; Kiechel, J. R.; Morgan, C. C.; Olliaro, P. L.; Taylor, W.R. J., The Efficacy and Safety of a New Fixed-dose Combination of Amodiaquine and Artesunate in Young African Children with Acute Uncomplicated Plasmodiumfalciparum. Malar. J. 2009, 8, 48.
De Pilla Varotti, F.; Botelho,A. C. C.; Andrade, A. A.; de Paula, R. C.; Fagundes, E. M. S.; Valverde, A.; Mayer, L. M. U.; Mendonca, J. S.; de Souza, M. V. N.; Boechat, N.; Krettli, A. U. Synthesis, Antimalalial Activity, and Intracellular Targets of MEFAS, a New Hybrid Compound Derived from Mefloquine and Artesunate. Antimicrob. Agents Chemother. 2008, 52, 3868-3874.

(Continued)

*Primary Examiner* — Kristin Vajda
(74) *Attorney, Agent, or Firm* — Ward and Smith, P.A.; Jeffrey W. Childers

(57) ABSTRACT

Anilide derivatives of the natural trioxane artemisinin were prepared and evaluated for antimalarial efficacy in *Plasmodium berghei*-infected mice. Selected anilides derivatives administered orally as one single-digit dose combined with mefloquine hydrochloride were completely curative, i.e., all 5 of the mice in the particular treatment group had no detectable parasitemia on day 30 post infection, gained as much weight by day 30 post infection as the control mice (no infection), and behaved normally.

9 Claims, 3 Drawing Sheets

(56) References Cited

OTHER PUBLICATIONS

Sagara, I.; Diallo, A. D.; Kone, M.; Coulibaly, M.; Diawara, S. I.; Guindo, O.; Maiga, H.; Niambele, M. B.; Sissoko, M.; Dicko, A.; Djimde, A.; Doumbo, 0. K. A Randomized Trial of Artesunate-mefloquine versus Artemether-lumefantrine for Treatment of Uncomplicated Plasmodium falciparum Malaria in Mali. Am. J. Trop. Med. Hyg. 2008, 79, 655-661.

Bhatt, K. M.; Samia, B. M.; Bhatt, S. M.; Wasunna, K. M. Efficacy and Safety of an Artesunate/mefloquine Combination, (Artequin) in the Treatment of Uncomplicated *P. falciparum* Malaria in Kenya. East Afr. Med. J. 2006, 83, 236-242.

Charman, S. A.; Arbe-Barnes, S.; Bathurst, I. C.; Brun, R.; Campbell, M.; Charman, W. N.; Chiu, F. C. K.; Chollet, J.; Craft, J.C.; Creek, D. J.; Dong, Y.; Matile, H.; Maurer, M.; Morizzi, J.; Nguyen, T.; Papastogiannidis, P.; Scheurer, C.; Shackleford, D. M.; Sriraghavan, K.; Stingelin, L.; Tang, Y.; Urwyler, H.; Wang, X.; White, K. L.; Wittlin, S.; Zhou, L.; Vennerstrom, J. L. Synthetic Ozonide Drug Candidate OZ439 Offers New Hope for a Single-dose Cure of Uncomplicated Malaria. PNAS, 2011, 108, 4400-4405.

Rosenthal, A. S.; Chen, X.; Liu, J. O.; West, D. C.; Hergenrother, P. J.; Shapiro, T. A.; Posner, G. H. Malaria-infected Mice are Cured by a Single Oral Dose of New Dimeric Trioxane Sulfones Which are Also Selectively and Powerfully Cytotoxic to Cancer Cells. J. Med. Chem. 2009, 52, 1198-1203.

Moon, D. K.; Tripathi, A.; Sullivan, D.; Siegler, M.A.; Parkin, S.; Posner, G. H. A Single, Low, Oral Dose of a 5-Carbon-linked Trioxane Dimer Orthoester Plus Mefloquine Cures Malaria-infected Mice. Bioorg. Med. Chem. Lett. 2011, 21, 2773-2775.

Posner, G. H.; Paik, I.-H.; Sur, S.; McRiner, A. J.; Borstnik, K.; Xie, S.; Shapiro, T. A. Orally Active, Antimalarial, Anticancer, Artemisinin-derived Trioxane Dimers with High Stability and Efficacy. J. Med. Chem. 2003, 46, 1060-1065.

Tenter, A. M., A. R. Heckeroth, and L. M. Weiss. 2000. Toxoplasma gondii: from animals to humans. Intl. J. Parasitol. 30:1217-1258.

Bachmann, S., J. Schroder, C. Bottmer, E. F., Torrey, and R.H. Yolken. 2005. Psychopathology in first-episode schizophrenia and antibodies to Toxoplasma gondii. Psychopathol. 38(2):87-90.

Berens, R. L., E. C. Krug, P. B. Nash, and T. J. Curiel. 1998. Selection and characterization of Toxoplasma gondii mutants resistant to artemisinin. J. Infect. Dis. 177: 1128-1131.

Georgiev, V. S. 1994. Management of toxoplasmosis. Drugs. 48(2): 179-188.

Chang, H. R. C. W. Jefford, and J.-C. Pechere. 1989. In vitro effects of three new 1,2,4-trioxanes (pentatroxane, thiahexatroxane, and hexatroxanone) on Toxoplasma gondii. Antimicrob. Agents Chemother. 33(10): 1748-1752.

Holfels, E., J. McAuley, D. Mack, W. K. Milhous, and R. McLeod. 1994. In vitro effects of artemisinin ether, cycloguanil hydrochloride (alone and in combination with sulfadiazine ), quinine sulfate, mefloquine, primaquine phosphate, trifluoperazine hydrochloride, and verapamil on Toxoplasma gondii. Antimicrob. Agents Chemother. 38(6):1392-1396.

Ou-Yang, K., E. C. Krug, J. J. Marr, and R. L. Berens. 1990. Inhibition of growth of Toxoplasma gondii by Qinghaosu and delivatives. Antimicrob. Agents Chemother. 34(10):1961-1965.

Lin A. J., D. L. Klayman, and W. K. Milhous. 1987. Antimalarial activity of new water-soluble dihydroartemisinin derivatives. J. Med. Chem. 30:2147-2150.

O'Neill P. M., Posner G. H. A medicinal chemistry perspective on artemisinin and related endoperoxides. J. Med. Chem. 2004, 47, 2945-2964.

Torrey EF, Bartko JJ, Lun ZR, Yolken RH. 200. Antibodies to Toxoplasma gondii in patients with schizophrenia: a meta-analysis. Schizophr. Bull. 33(3):729-736.

Jones-Brando, L., E. F. Torrey, and R. Yolken. 2003. Drugs used in the treatment of schizophrenia and bipolar disorder inhibit the replication of Toxoplasma gondii. Schizophr. Res. 62:237-244.

Menan, H., et al., Comparative Study of the Efficacy and Tolerability of Dihydroartemisinin-Piperaquine-Trimethoprim versus Artemether-Lumefantrine in the Treatment of Uncomplicated Plasmodium falciparum Malaria in Cameroon, Ivory Coast and Senegal, Malar. J. 2011, 10, 185-193.

Tohma, H., et al., Hypervalent Iodine(V)—Induced Asymmetric Oxidation of Sulfides to Sulfoxides Mediated by Reversed Micelles: Novel Nonmetallic Catalytic System, J. Org. Chem. 1999, 64, 3519-3523.

Haynes, R. K.; Fugmann, B.; Stetter, J.; Rieckmann, K.; Heilmann, H-D.; Chan, H-W.; Cheung, M-K.; Lam, W-L.; Wong, H-N.; Croft, S. L.; Vivas, L.; Rattray, L.; Stewart, L.; Peters, W.; Robinson, B. L.; Edstein, M. D.; Kotecka, B.; Kyle, D. E.; Beckermann, B.; Gerisch, M.; Radtke, M.; Schmuck, G.; Steinke, W.; Wollborn, U.; Schmeer, K.; Romer, A. Artemisone-A Highly Active Antimalarial Drug of the Artemisinin Class. Angew. Chem. Int. Ed. 2006, 45, 2082-2088.

Posner, G. H.; O'Dowd, H.; Caferro, T.; Cumming, J. N.; Ploypradith, P.; Xie, S.; Shapiro, T. A.; Antimalarial Synthetic Sulfone Trioxanes. Tetrahedron Lett. 1998, 39, 2273-2276.

Bachi, M. D.; Korshin, E. E.; Hoos, R.; Szpilman, A. M.; Ploypradith, P.; Xie, S.; Shapiro, T. A.; Posner, G. H. A Short Synthesis and Biological Evalutaion of Potent and Nontoxic Antimalarial Bridged Bicyclic ,8-Sulfonyl-Endoperoxides. J. Med. Chem. 2003, 46, 2516-2533.

Amewu, R.; Gibbon, P.; Mukhtar, A.; Stachulsk:i, A. V.; Ward, S. A.; Hall, C.; Rimmer, K.; Davies, J.; Vivas, L.; Bacsa, J.; Mercer, A. E.; Nixon, G.; Stocks, P.A.; O'Neill, P. M. Synthesis, in vitro and in vivo Antimalarial Assessment of Sulfide, Sulfone and Vinyl Amide-substituted 1,2,4-Trioxanes Prepared via Thiol-olefin Cooxgenation (TOCO) of Allylic Alcohols. Org. Biomol. Chem. 2010, 8, 2068-2077.

Jung, M.; Tak, J.; Chung, W-Y.; Park, K-K, Antiangiogenic Activity of Deoxoartemisinin Derivatives on Chorioallantoic Membrane. Bioorg. Med. Chem. Lett. 2006, 16, 1227-1230.

\* cited by examiner

MONOMERIC TRIOXANE AMIDE SULFUR COMPOUNDS

CROSS-REFERENCE TO RELATED APPLICATIONS

This application is a 35 U.S.C. §371 U.S. national phase entry of International Application No. PCT/US2012/03374 having an international filing date of Apr. 16, 2012, which claims the benefit of U.S. Provisional Application No. 51/475,758, filed Apr. 15, 2011, the content of each of the aforementioned applications is herein incorporated by reference in its entirety.

FEDERALLY SPONSORED RESEARCH OR DEVELOPMENT

This invention was made in part with United States Government support under AI 34885 awarded by the National Institutes of Health (NIH). The U.S. Government has certain rights in the invention.

BACKGROUND

Malaria parasites have developed widespread resistance to standard antimalarial drugs, such as chloroquine. Olliaro, P. L.; Boland, P. B. Clinical Public Health Implications of Antimalarial Drug Resistance. In Antimalarial Chemotherapy: Mechanisms of Action, Resistance, and New Directions in Drug Discovery; Rosenthal, P. J., Ed.; Humana Press: Totowa, N.J., 2001; pp. 65-83. Therefore, use of non-alkaloidal 1,2,4-trioxanes, such as artemisinin (qinghaosu 1, FIG. 1), combined with a standard alkaloidal antimalarial drug, is now recommended by the World Health Organization (WHO); Guidelines for the Treatment of Malaria; World Health Organization: Geneva, 2006.

This type of artemisinin combination therapy (ACT) features very rapid clearance of parasites by the trioxane, as well as prolonged antimalarial activity by an alkaloid, each with a different mechanism of action. Ashley, E. A.; White, N. J. Artemisinin-based Combinations. Curr. Opin. Infect. Dis. 2005, 18, 531-536; Adjuik, M., et al., Artesunate Combinations for Treatment of Malaria: Meta-analysis. Lancet 2004, 363, 9-17; Guthmann, J.-P., et al., High Efficacy of Two Artemisinin-based Combinations (Artesunate plus Amodiaquine and Artemether plus Lumefantrine) in Caala, Central Angola. Am. J. Trop. Med. Hyg. 2006, 75, 143-145; Myint, H. Y., et al., Efficacy and Safety of Dihydroartemisinin-piperaquine. Trans. R. Soc. Trop. Med. Hyg. 2007, 101, 858-866; Sirima, S. B., et al., The Efficacy and Safety of a New Fixed-dose Combination of Amodiaquine and Artesunate in Young African Children with Acute Uncomplicated Plasmodium falciparum. Malar. J. 2009, 8, 48; de Pilla Varotti, F., et al., Synthesis, Antimalarial Activity, and Intracellular Targets of MEFAS, a New Hybrid Compound Derived from Mefloquine and Artesunate. Antimicrob. Agents Chemother. 2008, 52, 3868-3874.

One current ACT drug features a three-day, six-dose adult regimen totaling approximately 480 mg of artemether (2b, FIG. 1) and 2,880 mg of the amino-alcohol lumefantrine. Sagara, I., et al., A Randomized Trial of Artesunate-mefloquine versus Artemether-lumefantrine for Treatment of Uncomplicated Plasmodium falciparum Malaria in Mali. Am. J. Trop. Med. Hyg. 2008, 79, 655-661. Another current ACT drug features a three-day, three-dose adult regimen totaling approximately 600 mg of sodium artesunate (2c, FIG. 1) and 750 mg of the quinoline antimalarial mefloquine. Bhatt, K. M., et al., Efficacy and Safety of an Artesunate/mefloquine Combination, (Artequin) in the Treatment of Uncomplicated P. falciparum Malaria in Kenya. East Afr. Med. J. 2006, 83, 236-242. Patient compliance with adhering to a repeated dose regimen, however, is often problematic. A recent study reports a two-day treatment of dihydroartemisinin-piperaquine phosphate-trimethoprim, which reported better patient compliance than the artemether-lumefantrine combination. Menan, H., et al., Comparative Study of the Efficacy and Tolerability of Dihydroartemisinin-Piperaquine-Trimethoprim versus Artemether-Lumefantrine in the Treatment of Uncomplicated Plasmodium falciparum Malaria in Cameroon, Ivory Coast and Senegal, Malar. J. 2011, 10, 185-193. Nevertheless, a single dose oral cure is highly desirable. A recent report features a single dose oral cure of P. berghei malaria-infected mice using synthetic 1,2,4-trioxolane ozonide OZ439 (3, FIG. 1). Charman, S. A., et al., Synthetic Ozonide Drug Candidate OZ439 Offers New Hope for a Single-dose Cure of Uncomplicated Malaria. PNAS, 2011, 108, 4400-4405.

Single-dose oral cures of P. berghei-infected mice have been reported previously using trioxane dimer sulfone carbamate 5 (FIG. 1), Rosenthal, A. S., et al., Malaria-infected Mice are Cured by a Single Oral Dose of New Dimeric Trioxane Sulfones Which are Also Selectively and Powerfully Cytotoxic to Cancer Cells. J. Med. Chem. 2009, 52, 1198-1203, using a dimer orthoester sulfone 6 (FIG. 1), Moon, D. K., et al., A Single, Low, Oral Dose of a 5-Carbon-linked Trioxane Dimer Orthoester Plus Mefloquine Cures Malaria-infected Mice. Bioorg. Med. Chem. Lett. 2011, 21, 2773-2775, and using trioxane monomer 4-fluoroanilide (12a). Woodard, L. E., et al., Malaria-Infected Mice Live Until at Least Day 30 After a New Monomeric Trioxane Combined with Mefloquine are Administered Together in a Single Low Oral Dose. J. Med. Chem. 2009, 52, 7458-7462. New single-dose, oral cures for malaria, however, remain of interest.

SUMMARY

In some aspects, the presently disclosed subject matter provides trioxane monomer anilides, which in some embodiments, comprise one or two sulfide, sulfoxide, or sulfone substituents on the anilide aromatic ring. In particular aspects, the presently disclosed trioxane sulfides (thioethers), in some embodiments, fully cured malaria-infected mice using only one single-digit oral dose combined with mefloquine hydrochloride. The presently disclosed subject matter provides the first example of an orally administered trioxane sulfide being more antimalarially efficacious than the corresponding sulfone.

In particular aspects, the presently disclosed subject matter provides a compound of formula (I):

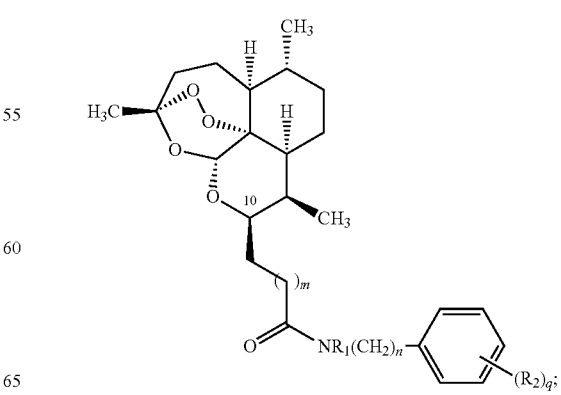

wherein: m is an integer selected from the group consisting of 0, 1, 2, and 3; n is an integer selected from the group consisting of 0, 1, 2, 3, and 4; q is an integer selected from the group consisting of 1, 2, 3, 4, and 5;

R$_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

each occurrence of R$_2$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl, —SR$_3$, —S(O$_2$)R$_3$, —S(O)R$_3$;

wherein R$_3$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

provided that if one occurrence of R$_2$ is halogen, then at least one occurrence of R$_2$ must be —SR$_3$, —S(O$_2$)R$_3$, —S(O)R$_3$; or an enantiomer, diastereomer, racemate or pharmaceutically acceptable salt, prodrug, or solvate thereof.

In certain aspects, the presently disclosed compounds of Formula (I) can be used for preventing, controlling or treating an infectious disease in a subject in need of treatment thereof. In particular aspects, the infectious disease includes a parasitic disease selected from the group consisting of a plasmodia parasite infection, a *T. gondii* infection, a trypanosome parasite infection, and a cryptosporidium parasite infection. In other aspects, the method of treatment further comprises administering to the subject a quinoline anti-malarial drug including, but not limited to, chloroquine, quinine, mefloquine, and primaquine, concurrently or sequentially with a compound of Formula (I).

In other aspects, the presently disclosed subject matter provides a method for treating a psychiatric disorder associated with a toxoplasma infection, such as schizophrenia, in a subject in need of treatment thereof, the method comprising administering to the subject a therapeutically-effective amount of a compound of Formula (I). In yet other aspects, the method further comprises administering to the subject one or more antipsychotic drugs selected from the group consisting of chlorpromazine (THORAZINE®), haloperidol (HALDOL®), fluphenazine (PROLIXIN®), thiothixene (NAVANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®) concurrently or sequentially with the compound of Formula (I).

In further aspects, the presently disclosed subject matter provides a method for treating cancer, including, but not limited to, leukemia, non-small cell lung cancer, colon cancer, central nervous system cancer, melanoma cancer, ovarian cancer, renal cancer, prostate cancer, and breast cancer, in a subject in need of treatment thereof, the method comprising administering to the subject a therapeutically-effective amount of a compound of Formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
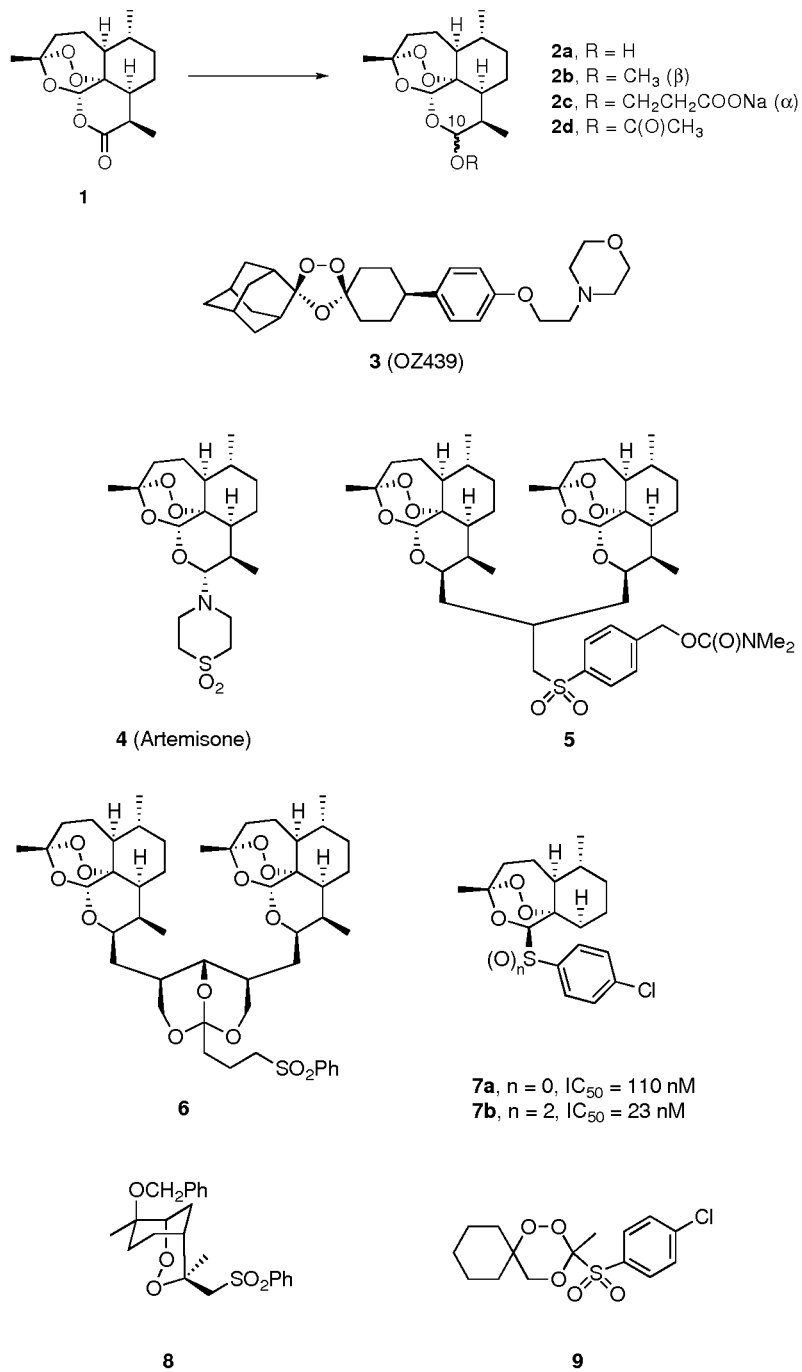
Figure 2:
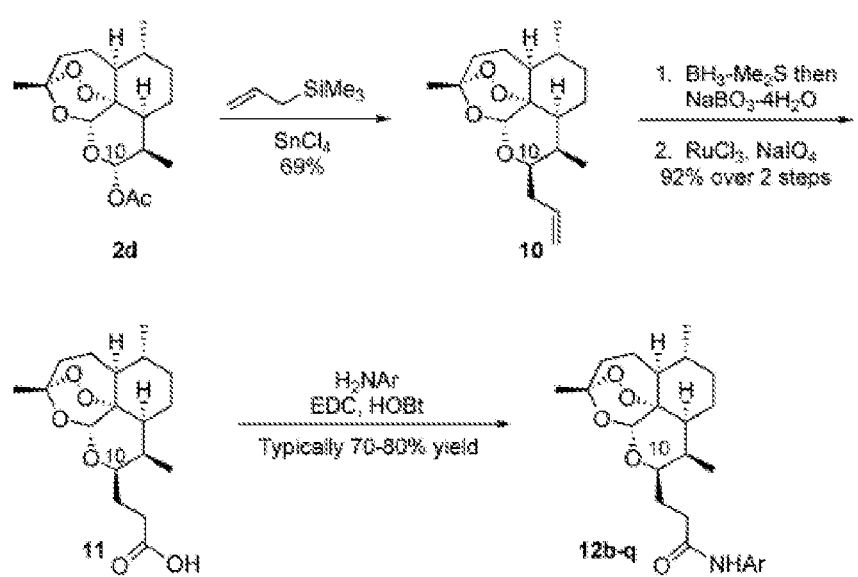
Figure 3:
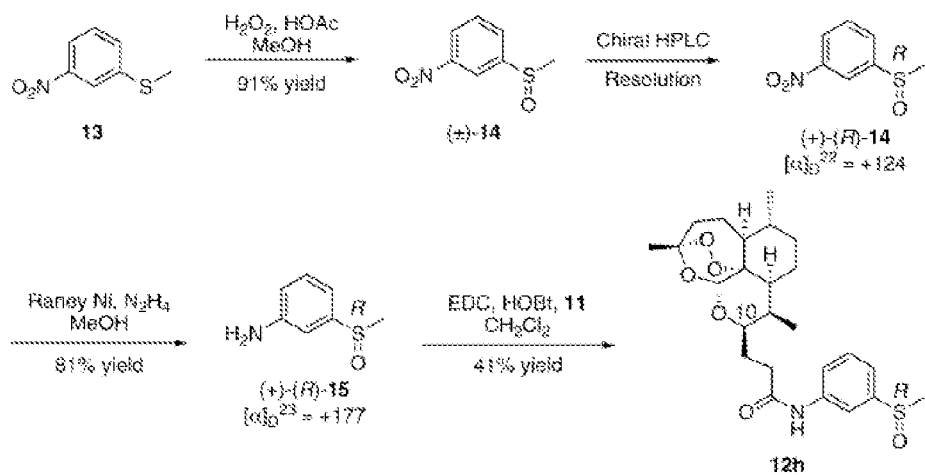

Having thus described the presently disclosed subject matter in general terms, reference will now be made to the accompanying Figures, which are not necessarily drawn to scale, and wherein:

FIG. 1 provides structures of artemisinin, artemisinin derivatives, and related compounds known in the art for treating malaria (Prior Art);

FIG. 2 is a representative synthesis scheme for the presently disclosed trioxane anilides; and FIG. 3 is a representative synthesis scheme for the presently disclosed trioxane sulfoxides.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Single-Digit Oral Dose of a Monomeric Trioxane Sulfide Combined with Mefloquine for Treating Malaria A. Representative Embodiments In some embodiments, the presently disclosed subject matter provides a compound of formula (I):

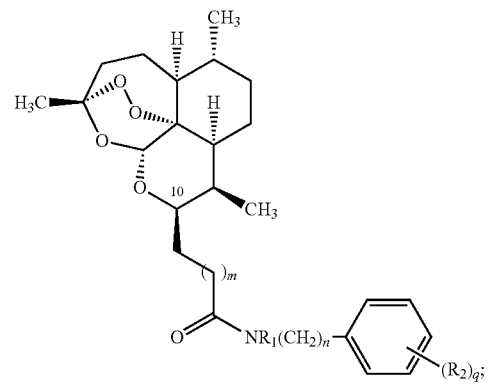

wherein: m is an integer selected from the group consisting of 0, 1, 2, and 3; n is an integer selected from the group consisting of 0, 1, 2, 3, and 4; q is an integer selected from the group consisting of 1, 2, 3, 4, and 5;

R₁ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl each occurrence of R₂ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl, —SR₃, —S(O₂)R₃, —S(O)R₃;

wherein R₃ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

provided that if one occurrence of R₂ is halogen, then at least one occurrence of R₂ must be —SR₃, —S(O₂)R₃, —S(O)R₃; or an enantiomer, diastereomer, racemate or pharmaceutically acceptable salt, prodrug, or solvate thereof.

In particular embodiments, the compound of Formula (I) is selected from the group consisting of:

(12c)

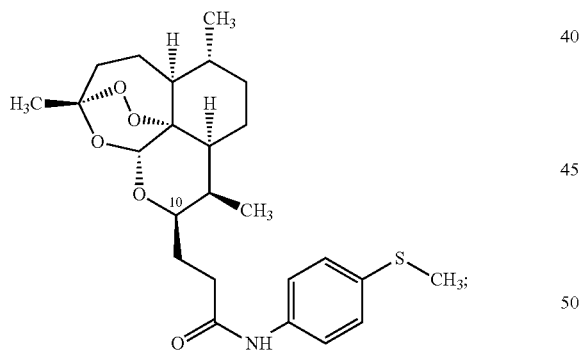

(12d)

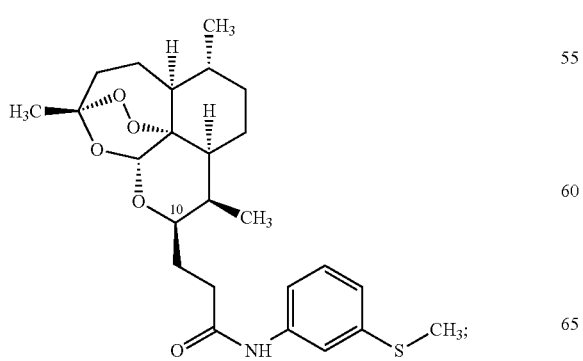

(12f)

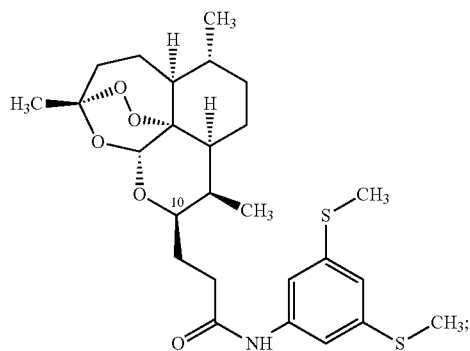

(12i)

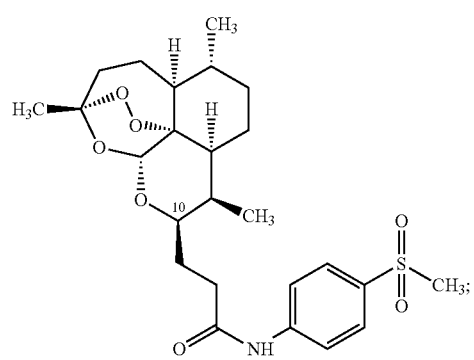

(12j)

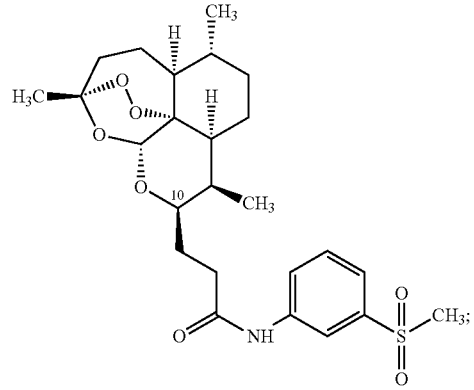

(12k)

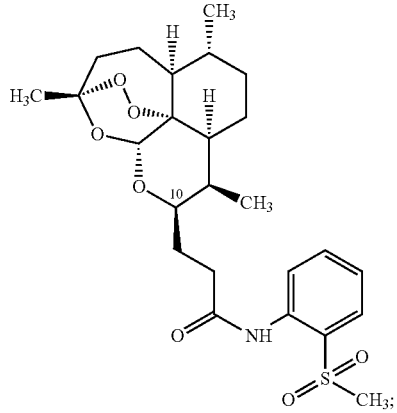

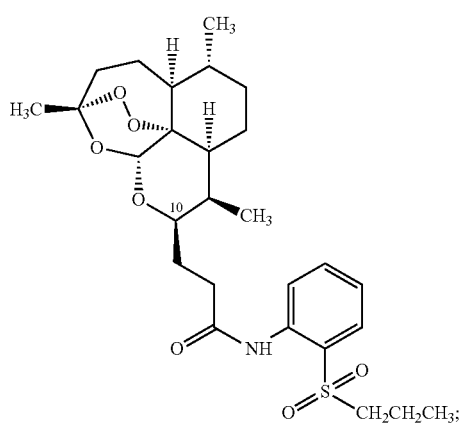
(12n)
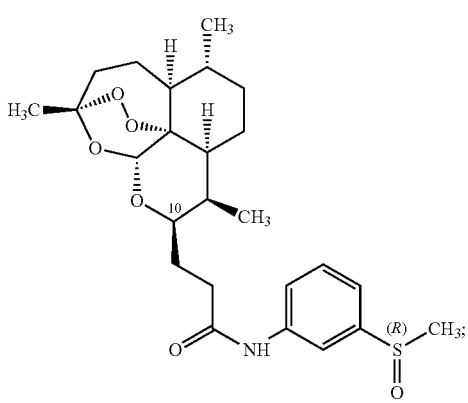
(12h)
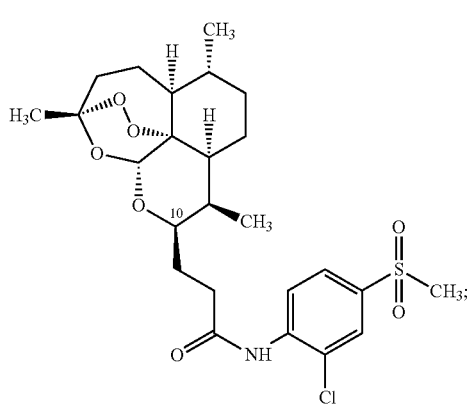
(12o)
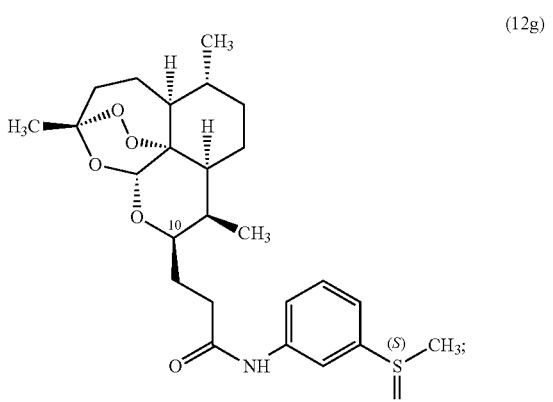
(12g)
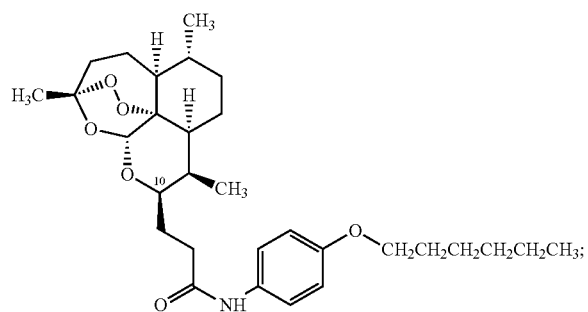
(12q)
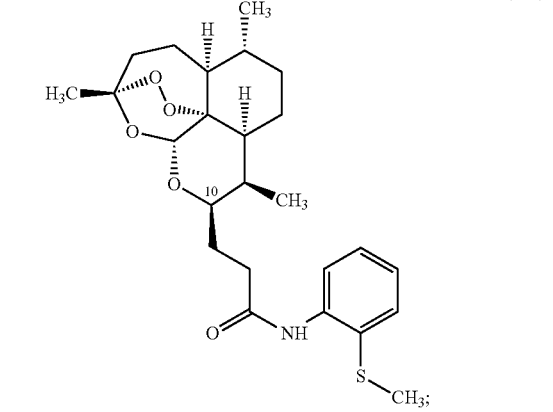
(12e)
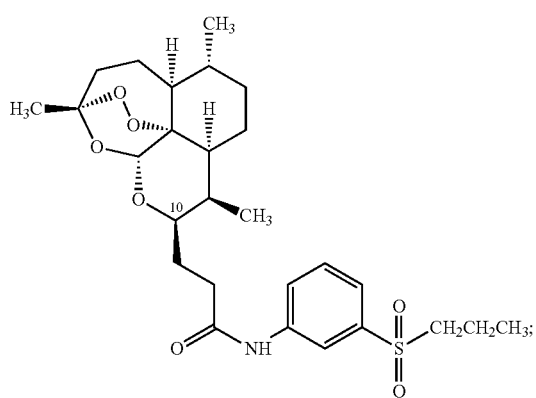
(12m)
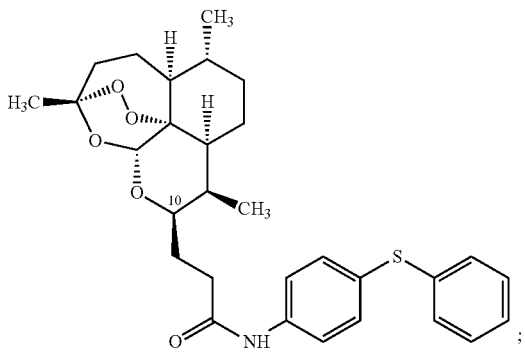

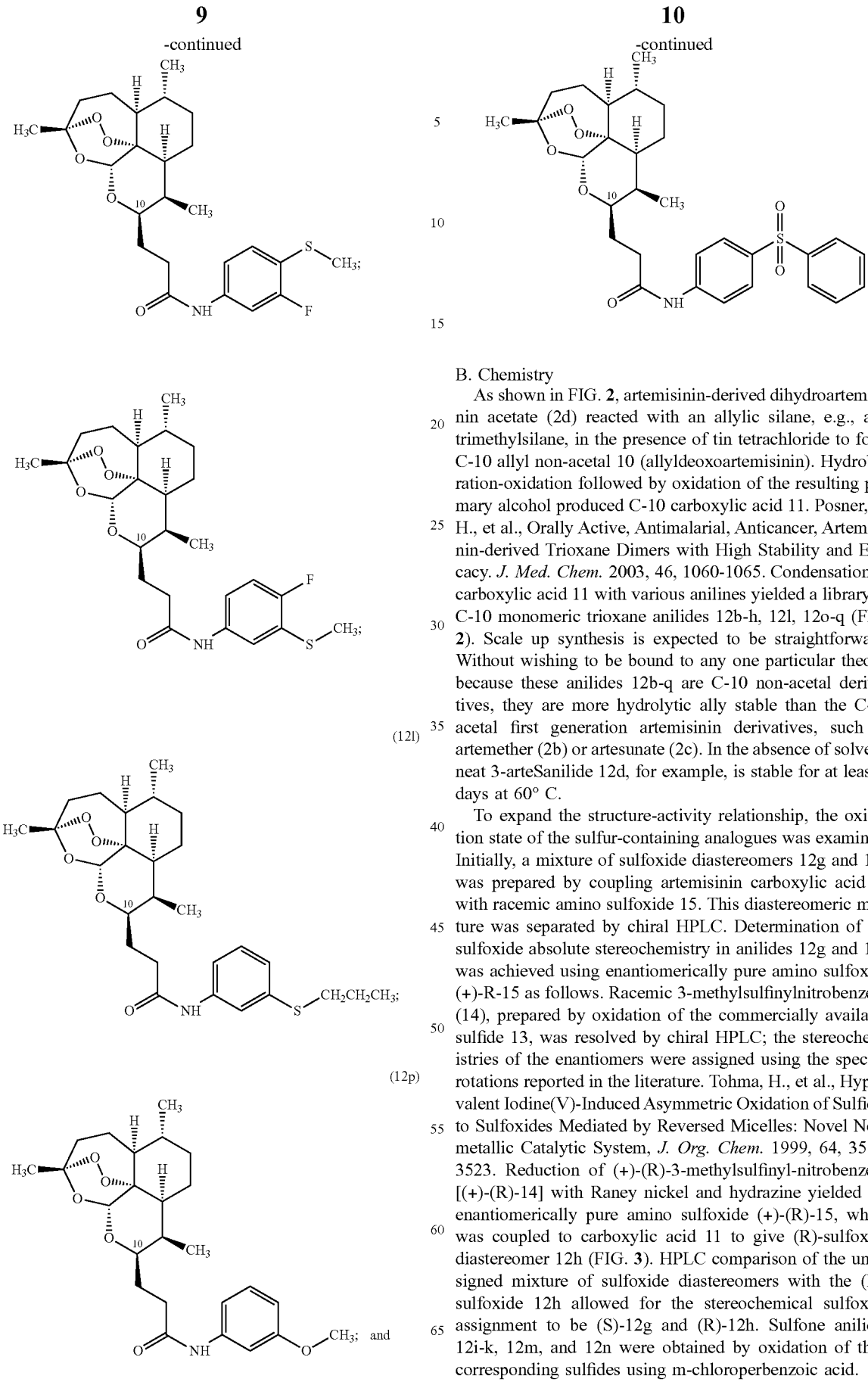

B. Chemistry

As shown in FIG. 2, artemisinin-derived dihydroartemisinin acetate (2d) reacted with an allylic silane, e.g., allyl trimethylsilane, in the presence of tin tetrachloride to form C-10 allyl non-acetal 10 (allyldeoxoartemisinin). Hydroboration-oxidation followed by oxidation of the resulting primary alcohol produced C-10 carboxylic acid 11. Posner, G. H., et al., Orally Active, Antimalarial, Anticancer, Artemisinin-derived Trioxane Dimers with High Stability and Efficacy. J. Med. Chem. 2003, 46, 1060-1065. Condensation of carboxylic acid 11 with various anilines yielded a library of C-10 monomeric trioxane anilides 12b-h, 12l, 12o-q (FIG. 2). Scale up synthesis is expected to be straightforward. Without wishing to be bound to any one particular theory, because these anilides 12b-q are C-10 non-acetal derivatives, they are more hydrolytic ally stable than the C-10 acetal first generation artemisinin derivatives, such as artemether (2b) or artesunate (2c). In the absence of solvent, neat 3-arteSanilide 12d, for example, is stable for at least 7 days at 60° C.

To expand the structure-activity relationship, the oxidation state of the sulfur-containing analogues was examined. Initially, a mixture of sulfoxide diastereomers 12g and 12h was prepared by coupling artemisinin carboxylic acid 11 with racemic amino sulfoxide 15. This diastereomeric mixture was separated by chiral HPLC. Determination of the sulfoxide absolute stereochemistry in anilides 12g and 12h was achieved using enantiomerically pure amino sulfoxide (+)-R-15 as follows. Racemic 3-methylsulfinylnitrobenzene (14), prepared by oxidation of the commercially available sulfide 13, was resolved by chiral HPLC; the stereochemistries of the enantiomers were assigned using the specific rotations reported in the literature. Tohma, H., et al., Hypervalent Iodine(V)-Induced Asymmetric Oxidation of Sulfides to Sulfoxides Mediated by Reversed Micelles: Novel Nonmetallic Catalytic System, J. Org. Chem. 1999, 64, 3519-3523. Reduction of (+)-(R)-3-methylsulfinyl-nitrobenzene [(+)-(R)-14] with Raney nickel and hydrazine yielded the enantiomerically pure amino sulfoxide (+)-(R)-15, which was coupled to carboxylic acid 11 to give (R)-sulfoxide diastereomer 12h (FIG. 3). HPLC comparison of the unassigned mixture of sulfoxide diastereomers with the (R)-sulfoxide 12h allowed for the stereochemical sulfoxide assignment to be (S)-12g and (R)-12h. Sulfone anilides 12i-k, 12m, and 12n were obtained by oxidation of their corresponding sulfides using m-chloroperbenzoic acid.

C. Biology: In Vivo Efficacies

Each trioxane (0.64 mg) was combined with mefloquine and dissolved in 0.10 mL of 7:3 Tween 80:ethanol and then diluted with 0.97 mL of distilled water for oral administration to 5-week old, approximately 20 gram C57BL/6J male mice (from the Jackson Laboratory) that were infected intraperitoneally on day 0 with *Plasmodium berghei*, ANKA malaria strain ($5 \times 10^7$ parasitized erythrocytes). Rosenthal, A. S., et al., Malaria-infected Mice are Cured by a Single Oral Dose of New Dimeric Trioxane Sulfones Which are Also Selectively and Powerfully Cytotoxic to Cancer Cells. *J. Med. Chem.* 2009, 52, 1198-1203. Each of four mice in a group was treated orally 24 hours post infection with a single dose of 0.20 mL [(0.20 mL/1.07 mL)×0.64 mg=0.12 mg] of diluted trioxane solution, corresponding to a dose of 6 mg/kg of trioxane, combined with 18 mg/kg of mefloquine hydrochloride. Alternatively, a single dose of 7.5 mg/kg of trioxane plus 15.0 mg/kg of mefloquine hydrochloride was used. The malariometrics used involved determining blood parasitemia levels, as well as monitoring the duration of animal survival compared to survival time of infected animals receiving no drug.

Three days after infection, an average of 10% blood parasitemia (Giemsa microscopy) was observed in the no-drug control group of mice. The average survival time of the malaria-infected animals receiving no drug was 6.8 days post infection. All of the infected mice in this study receiving the trioxane drug artemether (2b) plus mefloquine died on the average on day 18.8 post infection (Table 1, controls). Additionally, a single oral dose of artemether (6 mg/kg) plus lumefantrine (18 mg/kg) was not curative (see Table 1), with the mice dying an average of 12.5 days after infection. Monotherapy of mefloquine hydrochloride alone at a single oral dose of 18 mg/kg, prolonged the average survival time of the infected mice to 19.8 days. Lumefantrine alone, also at a single oral dose of 18 mg/kg, gave an average survival time of 21.5 days.

A widely accepted indication of complete cure (i.e., 100% efficacy) is survival of animals to day 30 post infection with no detectable malaria parasites in the animals' blood at that time. It is important to note that the combination of the standard trioxane drug artemether (2b), with either mefloquine hydrochloride or lumefantrine, was not curative (Table 1, controls). The average survival times of *P. berghei*-infected mice receiving a single, oral trioxane dose are shown in Table 1. The following conclusions emerge from these data. While 3-fluoroanilide 12b was not curative, administration of 3-methylthioether 3-arteSanilide 12d at a dose of 7.5 mg/kg plus 15 mg/kg mefloquine hydrochloride achieved mouse survival through day 30 after infection; however, all four of the surviving mice appeared sick and had considerable parasitemia levels (25-50%). Modification of the dose to 6 mg/kg 3-arteSanilide 12d and 18 mg/kg mefloquine resulted in a complete cure, with all mice in this group having gained as much weight by day 30 after infection (data not shown) as the uninfected control mice. In addition, 3-arteSanilide 12d is more efficacious than 4-arteSanilide 12c. From these data, the significance of thioether substitution at the 3-position of the phenyl ring emerged. Bis-sulfide 3,5-arteSSanilide 12f is partially curative at a single oral dose with all four mice alive on day 30 after infection but with one of the four mice possessing 5% parasitemia. Administration of 3-arteSanilide 12d and 3,5-arteSSanilide 12f at nontoxic single oral doses of 100 mg/kg (no mefloquine) resulted in prolonged mouse survival of the 3-arteSanilide 12d dosed mice, compared to essentially no increase in mouse longevity of bisulfide 3,5-arteSSanilide 12f treated mice. Replacing the sulfur atom in 12d with an oxygen atom afforded methyl ether 12p, which prolonged survival time to only 21.8 days after infection. This observation indicates the critical nature of the sulfur atom. In addition, the lipophilicity of 3-arteSanilide 12d was increased by lengthening the alkyl sulfide chain from methyl to n-propyl. 3-n-Propyl sulfide 12l, however, is much less efficacious than the curative methyl sulfide 3-arteSanilide 12d.

The presently disclosed subject matter also demonstrates the effect of oxidation states of the sulfur atom on antimalarial efficacy. Several sulfide- and sulfone-containing antimalarial trioxanes have been reported. For example, artemisone (4, FIG. 1), a semi-synthetic trioxane monomer sulfone, is currently in antimalarial clinical trials, Haynes, R. K., et al., Artemisone—A Highly Active Antimalarial Drug of the Artemisinin Class. *Angew. Chem. Int. Ed.* 2006, 45, 2082-2088. Trioxane dimer sulfone 5 (FIG. 1), Rosenthal, A. S., et al., Malaria-infected Mice are Cured by a Single Oral Dose of New Dimeric Trioxane Sulfones Which are Also Selectively and Powerfully Cytotoxic to Cancer Cells. *J. Med. Chem.* 2009, 52, 1198-1203, and trioxane dimer orthoester sulfone 6 (FIG. 1) cure malaria-infected mice, Moon, D. K., et al., A Single, Low, Oral Dose of a 5-Carbon-linked Trioxane Dimer Orthoester Plus Mefloquine Cures Malaria-infected Mice. *Bioorg. Med. Chem. Lett.* 2011, 21, 2773-2775, while synthetic trioxane monomer sulfone 7b (FIG. 1) is at least 4-times more antimalarially potent in vitro than the corresponding sulfide 7a (FIG. 1), Posner, G. H., et al., Antimalarial Synthetic Sulfone Trioxanes. *Tetrahedron Lett.* 1998, 39, 2273-2276. Synthetic sulfonyl endoperoxide 8 (FIG. 1) is strongly efficacious via oral administration in curing malaria-infected mice, Bachi, M. D., et al., A Short Synthesis and Biological Evaluation of Potent and Nontoxic Antimalarial Bridged Bicyclic β-Sulfonyl-Endoperoxides. *J. Med. Chem.* 2003, 46, 2516-2533, and synthetic 1,2,4-trioxane sulfone 9 (FIG. 1) is more antimalarially active in mice via oral administration than the corresponding sulfide. Amewu, R., et al., Synthesis, in vitro and in vivo Antimalarial Assessment of Sulfide, Sulfone and Vinyl Amide-substituted 1,2,4-Trioxanes Prepared via Thiol-olefin Co-oxygenation (TOCO) of Allylic Alcohols. *Org. Biomol. Chem.* 2010, 8, 2068-2077; Jung, M., et al., Anti-angiogenic Activity of Deoxoartemisinin Derivatives on Chorioallantoic Membrane. *Bioorg. Med. Chem. Lett.* 2006, 16, 1227-1230. Thus, it was surprising to find that trioxane sulfide 3-arteSanilide 12d combined with mefloquine cures malaria-infected mice, but that the corresponding sulfone 12g does not (see Table 1). In addition, 3-sulfoxide anilide trioxane diastereomers 12g and 12h have different antimalarial activities. 3-(R)-Sulfoxide 12h is partially curative and possesses antimalarial efficacy similar to that of 3-arteSanilide 12d. In contrast, the diastereomeric 3-(S)-sulfoxide 12g prolongs the average animal life span to only 23.0 days.

As further evidence of the complete cure of malaria-infected mice achieved by a single 6 mg/kg dose oral dose of 3-arteSanilide 12d plus 18 mg/kg mefloquine, blood from the cured mice in this group was inoculated into uninfected mice; no parasitemia was detected in the inoculated mice after 30 days.

TABLE 1

In Vivo Antimalarial Efficacy Using a Single Oral Dose of Trioxane Combined with Mefloquine Hydrochloride in *P. berghei* Infected Mice

| trioxane | single oral dose trioxane (mg/kg) | mefloquine hydro- chloride (mg/kg) | average survival (days) after infection | % suppres- sion of para- sitemia (on day 3 after infection) |
|---|---|---|---|---|
| 12b | 6 | 18 | 24.8 (16, 20, 30, 30)[a] | >99.9 |
| 12c | 7.5 | 15 | 16.3 (15, 15, 16, 19) | >99.9 |
| 12d | 6 | 18 | 30 (30, 30, 30, 30)[b] | >99.9 |
| 12d | 7.5 | 15 | 30 (30, 30, 30, 30)[c] | >99.9 |
| 12d | 100 | 0 | 15.0 (7, 7, 16, 30) | 97.2 |
| 12e | 6 | 18 | 27.0 (18, 30, 30, 30) | >99.9 |
| 12f | 6 | 18 | 30 (30, 30, 30, 30)[d] | >99.9 |
| 12f | 100 | 0 | 7.5 (7, 7, 8, 8) | 97.9 |
| 12g | 6 | 18 | 23.0 (16, 19, 28, 29) | >99.9 |
| 12h | 6 | 18 | 30 (30, 30, 30, 30)[e] | >99.9 |
| 12i | 7.5 | 15 | 22.5 (15, 16, 29, 30) | >99.9 |
| 12j | 7.5 | 15 | 15.5 (15, 15, 16, 16) | 99.9 |
| 12k | 7.5 | 15 | 22.8 (15, 16, 30, 30) | >99.9 |
| 12l | 6 | 18 | 23.0 (15, 18, 29, 30) | >99.9 |
| 12m | 6 | 18 | 11.0 (9, 11, 12, 12) | >99.9 |
| 12n | 6 | 18 | 21.8 (18, 18, 21, 30) | >99.9 |
| 12o | 7.5 | 15 | 24.5 (16, 21, 21, 30) | >99.9 |
| 12p | 6 | 18 | 21.8 (18, 18, 21, 30) | >99.9 |
| 12q | 7.5 | 15 | 15.0 (14, 15, 15, 16) | >99.9 |
| controls |  |  |  |  |
| Vehicle (no drug) | 0 | 0 | 6.8 (6, 7, 7, 7) | 0 |
| artemether (2b) | 6 | 18 | 18.8 (13, 16, 20, 26) | >99.9 |
| artemether (2b) | 7.5 | 15 | 19.8 (15, 21, 21, 22) | >99.9 |
| artemether (2b) | 6 | 18 (lume- fantrine) | 12.5 (12, 12, 13, 13) | >99.9 |
| mefloquine | 0 | 15 | 15.5 (14, 15, 15, 18) | >99.9 |
| mefloquine | 0 | 18 | 19.8 (16, 16, 20, 27) | >99.9 |
| lumefantrine | 0 | 18 | 21.5 (12, 22, 25, 27) | >99.9 |

[a] One of the two surviving mice on day 30 after infection had 2% parasitemia.
[b] No parasitemia detected on day 30 after infection.
[c] The four surviving mice had 25-50% parasitemia on day 30 after infection.
[d] Three mice were parasite-free on day 30, but one mouse had 5% parasitemia on day 30 after infection.
[e] One mouse had 1.8% parasitemia on day 30 after infection.

Biology: In Vitro Potencies. Prompted by the unexpected in vivo efficacy of 3-arteSanilide 12d, the in vitro the intrinsic antimalarial activity, free of host-mediated factors, was assayed of compounds that differ in the oxidative state of the sulfur atom (Table 2). In keeping with the rodent study, sulfide 12d is more potent than (S)-sulfoxide 12g or sulfone 12j.

TABLE 2

In Vitro Antimalarial Potencies of Trioxanes against *P. falciparum* (NF54) Parasites

| Trioxane | Antimalarial Activity[a] EC50, nM |
|---|---|
| 12d | 9.1 ± 0.57 |
| 12f | 6.5 ± 0.28 |
| 12g | 23 ± 1.3 |
| 12h | 29 ± 0.43 |
| 12j | 21 ± 1.1 |
| Control |  |
| Artemisinin (1) | 10 ± 1.1 |

[a] Values are M ± SD of at least four determinations; artemisinin activity is for concurrent controls.

In sum, 3-arteSanilide 12d not only cured malaria-infected mice, but also enabled them to gain as much weight as the control mice (no infection). Further, neither overt toxicity nor behavioral change attributable to trioxane administration was observed in any of the malaria-infected mice cured by 3-arteSanilide 12d combined with mefloquine hydrochloride.

TABLE 3

Calculated logP Values for Selected Compounds

|  | Ar | Calculated logP |
|---|---|---|
| 12a | 4-FPh (4-artefanilide) (Woodard et al. 2009) | 4.96 |
| 12b | 3-FPh (3-artefanilide) | 4.96 |
| 12c | 4-SMePh (4-arteSanilide) | 5.44 |
| 12d | 3-SMePh (3-arteSanilide) | 5.44 |
| 12e | 2-MeSPh (2-arteSanilide) | 5.44 |
| 12f | 3,5-(SMe)$_2$Ph [3,5-arteSSanilide] | 6.07 |
| 12g | 3-(S)-MeS(O)Ph | 3.55 |
| 12h | 3-(R)-MeS(O)Ph | 3.55 |
| 12i | 4-MeS(O)$_2$Ph[a] | 3.65 |
| 12j | 3-MeS(O)$_2$Ph[a] | 3.65 |
| 12k | 2-MeS(O)$_2$Ph[a] | 3.65 |
| 12l | 3-n-PrSPh | 6.22 |
| 12m | 3-n-PrS(O)$_2$Ph[a] | 5.32 |
| 12n | 2-n-PrS(O)$_2$Ph[a] | 5.34 |
| 12o | 2-Cl-4-MeS(O)$_2$Ph | 3.61 |
| 12p | 3-MeOPh | 4.66 |
| 12q | 4-n-HexOPh | 6.82 |

[a] Oxidized with mCPBA after EDC coupling of the corresponding aniline sulfide to the carboxylic acid 11.

D. Methods of Treatment

In some embodiments, the presently disclosed compounds of Formula (I) can be used for treating subjects infected with malaria or other parasitic infectious diseases including, but not limited to, toxoplasmic infection; subjects afflicted with psychiatric conditions associated with toxoplasmic infection; and subjects afflicted with cancer.

1. Methods of Treating Subject Infected with Malaria

Each year approximately 200-300 million people experience a malarial illness and over 1 million individuals die. In patients with severe and complicated disease, the mortality rate is between 20 and 50%. *Plasmodium* is the genus of protozoan parasites that is responsible for all cases of human malaria and *Plasmodium falciparum* is the species of parasite that is responsible for the vast majority of fatal malaria infections. Malaria has traditionally been treated with quinolines, such as chloroquine, quinine, mefloquine, and primaquine, and with antifolates, such as sulfadoxine-pyrimethamine. Unfortunately, most *P. falciparum* strains have now become resistant to chloroquine, and some, such as those in Southeast Asia, also have developed resistance to mefloquine and halofantrine; multidrug resistance also is developing in Africa.

The endoperoxides are a promising class of antimalarial drugs that may meet the dual challenges posed by drug-resistant parasites and the rapid progression of malarial illness. As discussed hereinabove, the first generation endoperoxides include natural artemisinin and several semi-synthetic derivatives. Artemisinin has been used successfully to treat malaria patients throughout the world, including those infected with both chloroquine-sensitive and chloroquine-resistant strains of *P. falciparum*.

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage, which is believed to be an essential moiety for antimalarial activity. In some embodiments, the presently disclosed subject matter provides a compound of Formula (I) useful for treating subjects infected with malaria.

Accordingly, the presently disclosed subject matter provides a method for treating a subject infected with malaria, the method comprising administering to a subject in need of treatment thereof, a compound of Formula (I) as disclosed herein. In some embodiments, the method further comprises administering to the subject a quinoline anti-malarial drug concurrently or sequentially with a compound of Formula (I). In particular embodiments, the quinoline anti-malarial drug is selected from the group consisting of chloroquine, quinine, mefloquine, and primaquine, or a pharmaceutically acceptable salt thereof. In more particular embodiments, the anti-malarial drug is mefloquine, or a pharmaceutically acceptable salt thereof.

2. Methods of Treating Other Parasitic Infectious Diseases

In some embodiments, the presently disclosed compounds of Formula (I) are useful for preventing, treating and controlling infections, including but not limited to toxoplasmic infection, and psychiatric conditions associated with toxoplasmic infection. *Toxoplasma gondii* (*T. gondii*) is an apicomplexan protozoan of world-wide medical importance. Humans are infected by *T. gondii* through contact with feces from infected cats, by the consumption of undercooked meat from infected animals, or by transmission from infected mother to fetus. This parasite can cause systemic infection and widespread organ damage in immunocompromised individuals and neonates. Infection of immunocompetent adults can result in fever and adenopathy. Tenter et al., 2000. Serological studies indicate that *T. gondii* could be associated with chronic neuropsychiatric diseases or behavioral abnormalities in some populations. Bachmann et al., 2005; Yolken et al., 2001.

Available medications for the prevention and treatment of toxoplasma infection show limited efficacy and have substantial side effects. Georgiev 1994. Published studies have indicated that the naturally occurring 1,2,4-trioxane artemisinin and artemisinin derivatives, such as artemether, originally developed for the treatment of malaria, have the ability to inhibit toxoplasma replication in vitro. Berens et al., 1998; Chang et al., 1989; Holfels et al., 1994; Ou-Yang et al., 1990.

While these trioxanes have a number of advantages in terms of rapid action and low levels of toxicity, they are limited in terms of absorption, bioavailability, and short half-life (i.e., easy hydrolysis into toxic dihydroartemisinin) Lin et al., 1987; O'Neill and Posner, 2004. Thus, what is needed are improved derivatives of artemisinin having not only rapid action and low levels of toxicity, but also better absorption, bioavailability, and longer half-lives for inhibiting the replication of *T. gondii*. Selected derivatives of artemisinin exhibiting in vitro efficacy against *T. gondii* are disclosed in published PCT patent application no. WO2008/127381 to Brando et al., which is incorporated herein by reference in its entirety. The artemisinin derivatives disclosed in WO2008/127381 also have been shown to inhibit the replication of chloroquine-sensitive *Plasmodium falciparum*.

Accordingly, in some embodiments, the presently disclosed subject matter provides methods of using the presently disclosed compounds of Formula (I) and compositions thereof for preventing, controlling or treating infectious diseases, including but not limited to, parasitic infectious diseases, such as *T. gondii* infection, trypanosome parasite infection, plasmodia parasite infection, and Cryptosporidium parasite infection.

Further, the evidence linking infection with *T. gondii* to the etiology of schizophrenia is well known. Torrey et al., 2007. Epidemiologic studies have indicated that infectious agents may contribute to some cases of schizophrenia. In animals, infection with *T. gondii* can alter behavior and neurotransmitter function. In humans, acute infection with *T. gondii* can produce psychotic symptoms similar to those displayed by persons with schizophrenia. Since 1953, a total of 19 studies of *T. gondii* antibodies in persons with schizophrenia and other severe psychiatric disorders and in controls have been reported; 18 reported a higher percentage of antibodies in the affected persons; in 11 studies the difference was statistically significant. Two other studies found that exposure to cats in childhood was a risk factor for the development of schizophrenia. Some medications used to treat schizophrenia inhibit the replication of *T. gondii* in cell culture. Jones-Brando et al., 2003. Establishing the role of *T. gondii* in the etiopathogenesis of schizophrenia may lead to new medications for its prevention and treatment.

Schizophrenia is a pervasive neuropsychiatric disease of uncertain cause that affects approximately 1% of the adult population in the United States and Europe. An increased occurrence of schizophrenia in family members of affected persons suggests that genetic factors play a role in its etiology, and some candidate predisposing genes have been identified. Environmental factors also are important. Epidemiologic studies, for example, have established that winter-spring birth, urban birth, and perinatal and postnatal infection are all risk factors for the disease developing in later life. These studies have rekindled an interest in the role of infectious agents in schizophrenia, a concept first proposed in 1896.

*T. gondii* is an intracellular parasite in the phylum Apicomplexa. Its life cycle can be completed only in cats and other fields, which are the definitive hosts. *T. gondii*, however, also infects a wide variety of intermediate hosts, including humans. In many mammals, *T. gondii* is known to be an important cause of abortions and stillbirths and to selectively infect muscle and brain tissue. A variety of neurologic symptoms, including incoordination, tremors, head-shaking, and seizures, has been described in sheep, pigs, cattle, rabbits, and monkeys infected with *T. gondii*. Humans may become infected by contact with cat feces or by eating undercooked meat. The importance of these modes of transmission may vary in different populations. Individual response to Toxoplasma infection is determined by immune status, timing of infection, and the genetic composition of the host and the organism.

Toxoplasma organisms have also been shown to impair learning and memory in mice and to produce behavioral changes in both mice and rats. Of special interest are studies showing that Toxoplasma-infected rats become less neophobic, leading to the diminution of their natural aversion to the odor of cats. These behavioral changes increase the chances that the rat will be eaten by a cat, thus enabling Toxoplasma to complete its life cycle, an example of evolutionarily driven manipulation of host behavior by the parasite.

In humans, toxoplasma is an important cause of abortions and stillbirths after primary infection in pregnant women. The organism also can cross the placenta and infect the fetus. The symptoms of congenital toxoplasmosis include abnormal changes in head size (hydrocephaly or microcephaly), intracranial calcifications, deafness, seizures, cerebral palsy, damage to the retina, and mental retardation. Some sequelae of congenital toxoplasmosis are not apparent at birth and may not become apparent until the second or third decade of life. Hydrocephalus, increased ventricular size, and cognitive impairment also have been noted in some persons with schizophrenia and other forms of psychosis.

Some cases of acute toxoplasmosis in adults are associated with psychiatric symptoms, such as delusions and hallucinations. Schizophrenia was first diagnosed in these patients, but later neurologic symptoms developed, which led to the correct diagnosis of Toxoplasma encephalitis.

Chlorpromazine (THORAZINE®) is the first antipsychotic medication used for schizophrenia, which was soon followed by other medications, such as haloperidol (HALDOL®), fluphenazine (PROLIXIN®), thiothixene (NAVANE®), trifluoperazine (STELAZINE®), perphenazine (TRILAFON®), and thioridazine (MELLARIL®). These medications have become known as "neuroleptics" because, although effective in treating positive symptoms (i.e., acute symptoms such as hallucinations, delusions, thought disorder, loose associations, ambivalence, or emotional lability), cause side effects, many of which affect the neurologic (nervous) system.

A new class of antipsychotics (atypical antipsychotics) was introduced after 1989. At clinically effective doses, no (or very few) of these neurological side effects, which often affect the extrapyramidal nerve tracts (which control such things as muscular rigidity, painful spasms, restlessness, or tremors) are observed. The first of the new class, clozapine (CLOZARIL®) is the only agent that has been shown to be effective where other antipsychotics have failed. Its use is not associated with extrapyramidal side effects, but it does produce other side effects, including possible decrease in the number of white cells, so the blood needs to be monitored every week during the first 6 months of treatment and then every 2 weeks to catch this side effect early if it occurs. Other atypical antipsychotics include risperidone (RISPERDAL®), olanzapine (ZYPREXA®), quetiapine (SEROQUEL®), ziprasidone (GEODON®), and aripiprazole (ABILITY®). The use of these medications has allowed successful treatment and release back to their homes and the community for many people suffering from schizophrenia.

Accordingly, in some embodiments, the presently disclosed subject matter provides a method for treating psychiatric disorders associated with toxoplasma infection including, but not limited to, schizophrenia, using the presently disclosed compounds of Formula (I) and compositions thereof alone or in combination with one or more antipsychotic drugs including, but not limited to, chlorpromazine (THORAZINE®), haloperidol (HALDOL®), fluphenazine (PROLIXIN®), thiothixene (NAVANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®).

3. Methods of Treating Cancer

Since the isolation of artemisinin, there has been a concerted effort by investigators to study other therapeutic applications of artemisinin and its derivatives. The National Institutes of Health reported that artemisinin is inactive against P388 leukemia (NCI Report on NSC 369397, tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays modest anticancer activity.

While artemisinin and its related derivatives demonstrate zero to slight antiproliferative and antitumor activity, it has been discovered that a class of artemisinin dimer compounds exhibits antiproliferative and antitumor activities that are, in vitro, equivalent to or greater than known antiproliferative and antitumor agents (U.S. Pat. No. 5,677,468 also incorporated herein by reference in its entirety for all purposes). Unfortunately, while the in vitro results of these artemisinin compounds are encouraging, these compounds do not appear to have as significant antitumor activity on the treatment of tumor cells in mice.

There is still a need, therefore, to develop stable artemisinin derivatives and structural analogs thereof having antimalarial, anticancer, antiproliferative, and antitumor activities that are equivalent to or greater than those of known antimalarial, anticancer, antiproliferative and antitumor agents, respectively. For example, selected artemisinin-related dimers, e.g., trioxane dimer sulfur compounds, having anticancer activity have been disclosed in international PCT patent application publication no. WO2010/009428, to Posner and Rosenthal, which is incorporated herein by reference in its entirety. Other artemisinin analogs, including trioxane dimers have been shown to exhibit anti-cancer activity. See, e.g., U.S. patent application publication nos. US2009/0291923, to Posner et al., published Nov. 26, 2009; US2006/0142377 to Posner et al., published Jun. 29, 2006; and US2002/0055528 to Posner et al., published May 9, 2002, each of which is incorporated herein by reference in its entirety.

Accordingly, in some embodiments, the presently disclosed subject matter provides a method for treating cancer in a subject in need of such treatment, by administering to the subject a therapeutically effective amount of the presently disclosed compounds of Formula (I). The cancer can include leukemia, non-small cell lung cancer, colon cancer, central nervous system cancer, melanoma cancer, ovarian cancer, renal cancer, prostate cancer, and breast cancer.

E. Pharmaceutical Compositions and Administration

In another aspect, the present disclosure provides a pharmaceutical composition including one or more compounds of Formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20th ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20th ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the disclosed trioxane sulfur monomer compounds may also be combined with include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

F. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$CH_2CH_2CH_2CH_2$—, —$CH_2CH$═$CHCH_2$—, —$CH_2CsCCH_2$—, —$CH_2CH_2CH(CH_2CH_2CH_3)CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

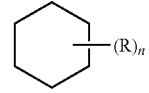

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

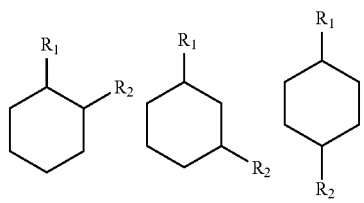

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

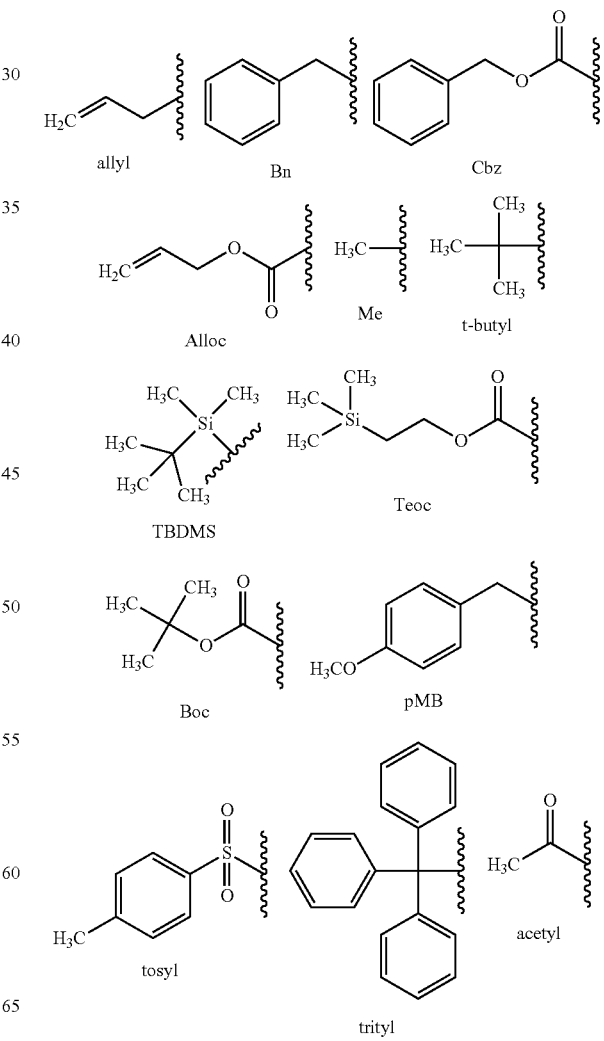

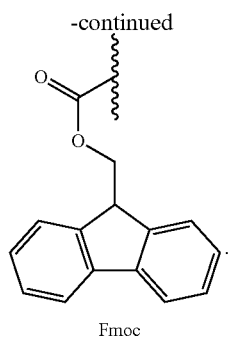

Fmoc

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Experimental Procedures $^1$H NMR (400 or 300 MHz), $^{13}$C NMR (100 or 75 MHz), and $^{19}$F NMR (282 MHz) spectra were recorded on a Bruker spectrometer using the residual solvent peak or trichlorofluoromethane as an internal standard. High resolution mass spectra from fast atom bombardment (HRMSFAB) were obtained using a VG70SE double focusing magnetic sector mass spectrometer (VG Analytical, Manchester, U.K., now-Micromass/Waters) equipped with a Cs$^+$ ion gun (28 kV at 2 μA), an off-axis multiplier, and a MSS data system (MasCom, Bremen, Germany). The resolution of the instrument was set at 10 000 (100 ppm peak width). Samples were mixed with m-nitrobenzyl alcohol matrix deposited on the target of a direct insertion probe for introduction into the source. For accurate mass measurements, a mass scan range was employed with the matrix containing 10% polyethylene glycol (PEG) or polyethylene glycol, monomethyl ether (PEGMME) mass calibrant. Low resolution mass spectra (electrospray ionization) were acquired on an Agilent Technologies 6130 quadrupole spectrometer coupled to an Agilent Technologies 1200 series HPLC instrument. High resolution mass spectra from electrospray ionization (HRMS-ESI) were obtained on an Agilent Technologies 1200 series dual absorbance detector HPLC system equipped with a Phenomenex Luna 75 mm×3 mm, C18, 3 μm column at 45° C. (UV detection at 220 nm, BW 8 nm, and 254 nm BW 8 nm, flow rate of 0.8 mL/min (increasing), injection volume of 1.0 μL, sample solvent of 100% methanol, sample concentration of approximately 0.01 mg/mL, mobile phase A consisting of water with 0.1% acetic acid, mobile phase B consisting of acetonitrile with 0.1% acetic acid) coupled to a Agilent 6210 time-of-flight mass spectrometer (ion source, Duel ESI; min range, 115 m/z; max range, 1400 m/z; scan rate, 0.9 s; gas temp, 340° C.; gas flow, 10 L/min; nebulizer, 50 PSI; ion polarity, positive; VCap, 3500 V; fragmentor, 175 V; skimmer1, 65 V; OctopoleRFPeak, 250 V; ref mass, enabled (Agilent P/N G1969-85001). Data were analyzed using Agilent Masshunter Workstation Data Acquisition (version B.02.00, patch 1,2,3) and Agilent Masshunter Qualitative Analysis (version B.02.00, build 2.0.197.7, patch 3). Fourier transform-infrared (FT-IR) experiments were performed on a Bruker Vector 22 instrument. Optical rotation values were obtained using a 100 mm quartz cell on a JASCO P-1010 polarimeter with a 589 nm source. The purity of analogues 12b-q was determined to be >95% by HPLC. HPLC data were acquired using a Varian ProStar 210 two-pump system with a ProStar 325 dual wavelength detector set at 215 and 254 nm Chiral Columns ((S,S)-Whelk-0 5/100 Kromasil 25 cm×4.6 cm i.d. and RegisCell 25 cm×4.6 cm i.d.) were purchased from Regis Technologies. The log P values were calculated by using Marvin-Sketch and a calculator plug-in by ChemAxon Kft.

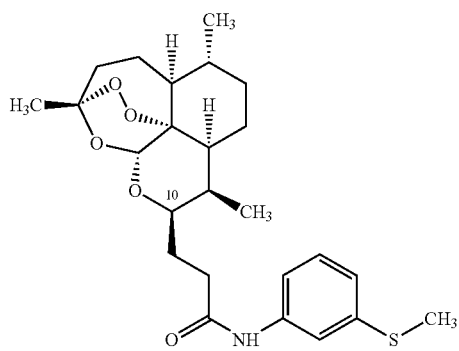

Synthesis of 3-ArteSanilide 12d. To an oven-dried 10 mL round-bottom flask were added carboxylic acid monomer 11 (15 mg, 0.044 mmol), EDC (9.3 mg, 0.048 mmol), HOBt (6.5 mg, 0.048 mmol), and $CH_2Cl_2$ (1 mL). The mixture was stirred for 1 h before commercially available 3-aminothioanisole (6.5 μL, 0.053 mmol) was added dropwise and stirred for an additional 18 h at room temperature until TLC analysis indicated consumption of starting material. The reaction was quenched with brine (3 mL) and the appropriate layer extracted with $CH_2Cl_2$ (3×3 mL). The resulting organic extracts were dried over $MgSO_4$ and concentrated in vacuo. The crude product was purified by preparative thin layer chromatography (silica gel, 40% ethyl acetate/hexanes) to afford 12d as a colorless, amorphous solid (88% yield, 18.0 mg, 0.039 mmol). FT-IR (thin film, cm$^{-1}$) 3331, 2941, 1670, 1550, 1466, 1384, 1301, 1299, 1106, 1053. $^1$H NMR (400 MHz, CDCl$_3$) δ 7.78 (bs, 1H), 7.57 (s, 1H), 7.25 (d, J=8.8 Hz, 1H), 7.19 (t, J=8.0 Hz, 1H), 6.97 (t, J=7.6 Hz, 1H), 5.35 (s, 1H), 4.17 (m, 1H), 2.77-2.59 (m, 2H), 2.48 (m, 1H), 2.47 (s, 3H), 2.33 (m, 1H) 2.05-1.76 (m, 5H), 1.62 (m, 2H), 1.49-1.22 (m, 5H), 1.39 (s, 3H), 0.95 (d, J=5.6 Hz, 3H), 0.89 (d, J=7.6 Hz, 3H). $^{13}$C NMR (100 MHz, CDCl$_3$) 171.4, 139.3, 138.7, 129.0, 122.0, 117.3, 116.3, 103.4, 88.9, 81.1, 76.0, 52.3, 44.4, 37.4, 36.5, 36.0, 34.4, 30.2, 26.1, 26.1, 24.9, 24.6, 20.2, 15.6, 13.1. [α]$_D^{26}$ +51.3 (c 0.72, CHCl$_3$). HRMS m/z for $C_{25}H_{36}NO_6$ (M+H)$^+$ calculated 463.2392, found 463.2390.

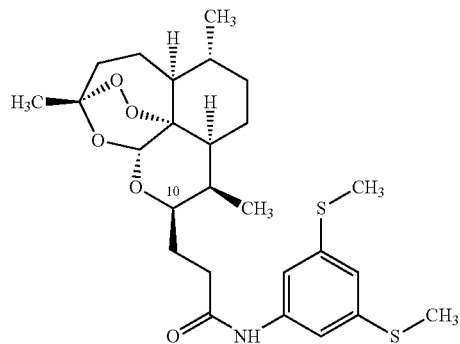

Synthesis of 3,5-ArteSanilide 12f. To an oven-dried 10 mL round-bottom flask was added carboxylic acid monomer 11 (15 mg, 0.044 mmol), EDC (9.3 mg, 0.048 mmol), HOBt (6.5 mg, 0.048 mmol), and 3,5-bis(methylsulfanyl)aniline (9.8 mg, 0.053 mmol). The contents were dissolved in $CH_2Cl_2$ (1 mL) and stirred for 18 h at room temperature until TLC analysis indicated consumption of starting material. The reaction was quenched with brine (3 mL), and the appropriate layer was extracted with $CH_2Cl_2$ (3×3 mL). The resulting organic extracts were dried over $MgSO_4$ and concentrated in vacuo. The crude product was purified by preparative thin layer chromatography (silica gel, 40% ethyl acetate/hexanes) to afford 12d as a colorless, amorphous solid (61% yield, 13.6 mg, 0.027 mmol). FTIR (thin film, cm$^{-1}$) 3333, 2989, 1661, 1541, 1451, 1368, 1289, 1204, 1045, 1008. $^1$H NMR (400 MHz, CDCl$_3$) δ 7.71 (bs, 1H), 7.60 (s, 2H), 7.43 (s, 1H), 5.32 (s, 1H), 4.20 (m, 1H), 2.79-2.49 (m, 2H), 2.44 (m, 1H), 2.40 (s, 6H), 2.32 (m, 1H) 2.21-1.70 (m, 4H), 1.59 (m, 3H), 1.42-1.22 (m, 5H), 1.42 (s, 3H), 0.94 (d, J=6.0 Hz, 3H), 0.90 (d, J=7.9 Hz, 3H). $^{13}$C NMR (100 MHz, CDCl$_3$) 171.0, 138.8, 138.3, 128.0, 121.0, 116.4, 116.1, 100.8, 87.5, 80.2, 75.5, 52.1, 50.4, 47.2, 38.1, 36.6, 365.7, 34.2, 30.7, 26.2, 25.8, 23.1, 22.2, 20.1, 16.0, 12.9. [α]$_D^{23}$ +43 (c 0.40, CHCl$_3$). HRMS m/z calculated for $C_{28}H_{36}S_2NO_5$ (M+H)$^+$ 508.7136, found 508.7139.

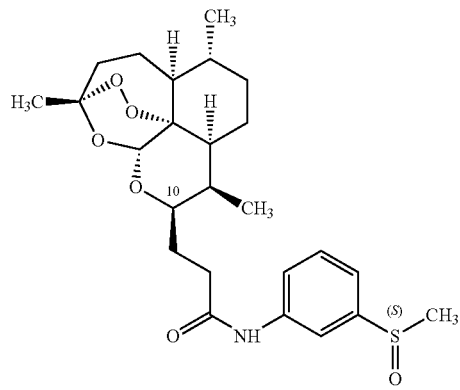

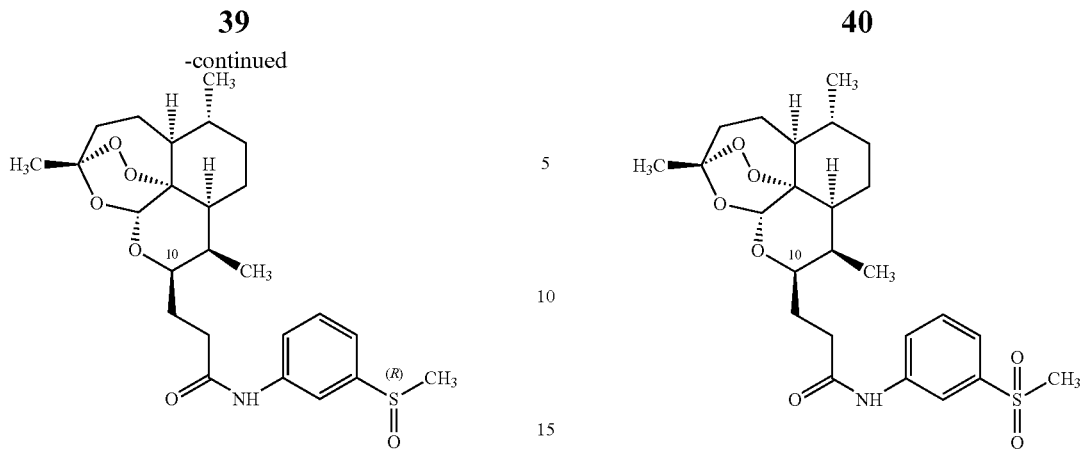

Synthesis of 3-Methyl Sulfoxides 12g and 12h. Carboxylic acid 11 (15 mg, 0.044 mmol), EDC (9.3 mg, 0.048 mmol), and HOBt (6.5 mg, 0.048 mmol) were dissolved in CH$_2$Cl$_2$ (2 mL) in a 10 mL round-bottom flask. The solution was stirred for 1 h at room temperature before (±)-15 (8.1 mg, 0.053 mmol) was added. The mixture was allowed to stir for 48 h before it was quenched with brine (3 mL) and extracted with CH$_2$Cl$_2$ (3×4 mL). The combined organic layers were dried with MgSO$_4$ and concentrated under reduced pressure. The resulting crude oil was purified by preparative thin layer chromatography (silica gel, 100% EtOAc) to afford a 1:1 diastereomeric mixture of 12g and 12h (51% yield, mg, 10.5 mg, 0.022 mmol). This mixture was separated by HPLC (Regis Whelk-01 (S,S); 10-50% IPA in hexanes; detection wavelength 254 nm; flow rate of 2.5 mL/min); tr=115.1 min (S)-sulfoxide 12g and 128.1 min (R)-sulfoxide 12h. Spectral data are shown below.

Analytical Data of 3-(S)-Sulfoxide 12g. Amorphous, white solid. $^1$H NMR (400 MHz, CDCl$_3$) δ 8.50 (d, J=8.5 Hz, 1H), 7.82 (dd, J=7.4, 1.2 Hz, 1H), 7.60 (t, J=7.2 Hz, 1H), 7.24 (t, J=7.2 Hz, 1H), 5.32 (s, 1H), 4.20 (dd, J=9.1, 6.8 Hz, 1H), 3.10 (m, 2H), 2.75 (s, 3H), 2.73 (m, 2H), 2.51 (m, 1H), 2.31 (td, J=14.1, 3.6 1H), 2.04 (m, 2H), 1.71 (m, 4H), 1.70 (m, 4H), 1.36 (s, 3H), 0.94 (d, J=6 Hz, 3H), 0.88 (d, J=7.5 Hz, 3H). $^{13}$C NMR (100 MHz, CDCl$_3$) δ 172.2, 137.3, 134.9, 129.9, 125.8, 123.6, 123.0, 103.7, 89.0, 87.1, 75.4, 57.8, 48.8, 40.0, 36.6, 36.3, 36.1, 34.4, 30.2, 26.1, 24.9, 24.7, 20.2, 16.1, 13.0. [α]$_D^{24}$ +29 (0.12, CHCl$_3$); [α]$_D^{24}$ +44 (c 0.12, CHCl$_3$). HRMS m/z calculated for C$_{25}$H$_{36}$SNO$_6$ (M+H)$^+$ 478.2263, found 478.2266.

Analytical Data of 3-(R)-Sulfoxide 12h. Amorphous, white solid. $^1$H NMR (300 MHz, CDCl$_3$) δ 8.28 (bs, 1H), 7.88 (m, 1H), 7.75 (d, J=6.9 Hz, 1H) 7.47 (t, J=7.8 Hz, 1H), 7.35 (d, J=7.8 Hz, 1H), 5.35 (s, 1H), 4.22 (m, 1H), 2.79-2.46 (m, 5H), 2.74 (s, 3H), 2.34 (td, J=14.4, 3.9 Hz, 1H), 2.09-1.79 (m, 5H), 1.69-1.55 (m, 2H), 1.50-1.20 (m, 3H), 1.38 (s, 3H), 0.96 (d, J=5.7 Hz, 3H), 0.91 (d, J=7.5 Hz, 3H). $^{13}$C NMR (100 MHz, CDCl$_3$) δ 172.0, 137.4, 134.9, 129.9, 125.6, 123.3, 122.9, 103.9, 89.3, 87.0, 75.4, 57.2, 48.6, 39.8, 36.8, 36.3, 36.0, 34.5, 30.1, 26.3, 24.8, 24.3, 20.2, 16.1, 13.0. [α]$_D^{24}$ +61 (c 0.12, CHCl$_3$). HRMS m/z calculated for C$_{25}$H$_{36}$SNO$_6$ (M+H)$^+$ 478.2263, found 478.2265.

Synthesis of 3-Sulfone 12j. 3-ArteSanilide 12d (16.1 mg, 0.035 mmol) was dissolved in CH$_2$Cl$_2$ (1.5 mL) to which mCPBA (≤77%, 17.1 mg, 0.077 mmol) was added and stirred for 2.5 h. The reaction was quenched with NaHCO$_3$ (aq, 2 mL) and the appropriate layer extracted with CH$_2$Cl$_2$ (3×3 mL). The organic layers were washed with saturated NaHCO$_3$ and saturated NaHSO$_3$, dried with MgSO$_4$, concentrated in vacuo, and purified by preparative thin layer chromatography (silica gel, 60%, ethyl acetate/hexanes) to yield 12j as a colorless, amorphous solid (94% yield, 16.2 mg, 0.033 mmol). FTIR (thin film, cm$^{-1}$) 3298, 2921, 1666, 1570, 1531, 1444, 1372, 1296, 1124, 1092, 1058, 1008. $^1$H NMR (300 MHz, CDCl$_3$) δ 8.32 (bs, 1H), 8.11 (s, 1H), 7.95 (d, J=8.2 Hz, 1H), 7.65 (d, J=7.9 Hz, 1H), 7.50 (t, J=8.0 Hz, 1H), 5.36 (s, 1H), 4.19 (m, 1H), 3.06 (s, 3H), 2.79-2.50 (m, 3H), 2.33 (m, 1H), 2.04-1.58 (m, 6H), 1.46-1.16 (m, 7H), 1.38 (s, 3H), 0.96 (d, J=9.0 Hz, 3H), 0.83 (d, J=6.8 Hz, 3H). $^{13}$C NMR (75 MHz, CDCl$_3$) δ 171.9, 138.6, 135.3, 129.9, 128.8, 126.4, 123.7, 122.9, 103.3, 89.0, 87.1, 75.4, 57.8, 54.6, 43.8, 37.4, 36.5, 36.1, 34.4, 30.2, 26.1, 24.9, 24.4, 20.2, 12.9. [α]$_D^{22}$ +41 (c 0.19, CHCl$_3$). HRMS m/z calculated for C25H36NO7S (M+H)$^+$ 494.2212, found 494.2216.

Synthesis of 3-artefanilide 12b. A flame dried 5 mL RBF was charged carboxylic acid monomer 11 (30 mg, 0.088 mmol), EDC (27 mg, 0.14 mmol), and HOBt (15 mg, 0.11 mmol). CH$_2$Cl$_2$ (2.5 mL) was then added and the mixture was stirred for an hour at which time, 3-fluoroaniline (32 μL, 0.33 mmol) was added by syringe. The reaction was allowed to stir at room temperature for 3 hours. It was then quenched with 1N HCl, extracted with dichloromethane (3×5 mL), washed with brine, dried over magnesium sulfate and evaporated. The crude product was purified by preparative thin layer chromatography (silica gel, 40% EtOAc/Hexanes) to afford 12b as an amorphous, white solid (20 mg, 0.050 mmol, 57%). FT-IR (thin film, cm$^{-1}$) 3330, 2962, 2876, 1700, 1679, 1614, 1542, 1491, 1441, 1376, 1318, 1275, 1261, 1189, 1138, 1116, 1095, 1052, 1008. $^1$H-NMR (400 MHz, CDCl$_3$) δ 8.06 (bs, 1H), 7.51 (m, 1H), 7.20 (m, 2H), 6.75 (m, 1H), 5.35 (s, 1H), 4.17 (m, 1H), 2.73 (m, 1H), 2.61 (m, 1H), 2.50 (m, 1H), 2.37-2.29 (m, 1H), 2.04-1.79 (m, 5H), 1.66-1.58 (m, 2H), 1.49-1.22 (m, 7H, including singlet at 1.37), 0.96-0.94 (m, 4H), 0.88 (d, 3H, J=7.6 Hz); $^{13}$C-NMR (100 MHz, CDCl$_3$) δ 171.5, 162.9 (d, J$_{C-F}$=24.2 Hz), 139.7 (d, J$_{C-F}$=11 Hz), 129.9 (d, J$_{C-F}$=8 Hz), 115.0, 110.6 (d, J$_{C-F}$=22 Hz), 107.4 (d, J$_{C-F}$=11 Hz), 107.1 (d, J$_{C-F}$=10 Hz), 103.5, 88.9, 81.1, 76.1 (d, J$_{C-F}$=8 Hz), 52.3, 44.3, 37.4, 36.5, 36.1, 34.4, 30.2, 26.0 (d, J$_{C-F}$=5 Hz), 24.9 (d, J$_{C-F}$=8 Hz), 24.6, 20.1, 13.0; $^{19}$F NMR (282 MHz, CDCl$_3$) δ −112.3; $[α]_D^{24}$=+25 (c=0.14, CHCl$_3$). HRMS (FAB) m/z calculated for C$_{24}$H$_{33}$FNO$_5$ (M+H)$^+$434.2343, found 434.2344.

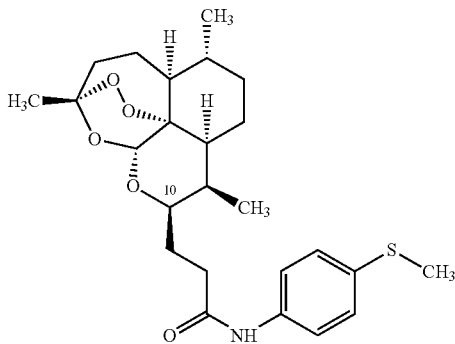

Synthesis of 4-arteSanilide 12c. To a flame dried 10 mL round bottom flask was added carboxylic acid monomer 11 (16 mg, 0.047 mmol), EDC (9.9 mg, 0.052 mmol), HOBt (7.0 mg, 0.052 mmol), and CH$_2$Cl$_2$ (1 mL). The reaction was stirred for 1 hour before commercially available 4-aminothioanisole (6.9 μL, 0.056 mmol) was added dropwise and stirred for an additional 18 hours at room temperature until TLC analysis indicated consumption of starting material. The reaction was quenched with brine (3 mL), and extracted with CH$_2$Cl$_2$ (3×3 mL). The resulting organic extracts were dried over MgSO$_4$ and concentrated in vacuo. The crude product was purified by preparative thin layer chromatography (silica gel, 40% ethyl acetate/hexanes) to afford 12c as a colorless, amorphous solid as a colorless, amorphous solid (83% yield, 18.0 mg, 0.039). FT-IR (thin film, cm$^{-1}$) 3313, 2939, 2874, 1663, 1614, 1543, 1509, 1451, 1406, 1377, 1212, 1124, 1091, 1055, 1012, 876, 835, 754 cm$^{-1}$; $^1$H NMR (400 MHz, CDCl$_3$) δ 7.72 (bs, 1H), 7.48 (d, J=8.8 Hz, 2H), 7.22 (d, J=8.8 Hz, 2H), 5.34 (s, 1H), 4.18 (m, 1H), 2.73 (m, 1H), 2.63-2.46 (m, 2H), 2.46 (m, 3H), 2.33 (td, J=14.4, 4.0 Hz, 1H), 2.05-1.79 (m, 5H), 1.68-1.58 (m, 5H), 1.45-1.22 (m, 2H), 1.39 (s, 3H), 0.96 (d, J=6 Hz, 3H), 0.89 (d, J=7.6 Hz, 3H); $^{13}$C NMR (100 MHz, CDCl$_3$) δ 171.3, 157.9, 139.4, 134.2, 123.8, 121.6, 115.3, 103.4, 88.9, 81.1, 76.1, 52.3, 44.3, 37.4, 36.7, 35.2, 34.3, 30.9, 30.1, 26.0, 24.8, 24.6, 19.9, 19.3, 13.0; $[α]_D^{22}$=+60 (c=0.47, CHCl$_3$); HRMS m/z calculated C$_{25}$H$_{36}$SNO$_5$ (M+H)$^-$ 463.2392, found 463.2388.

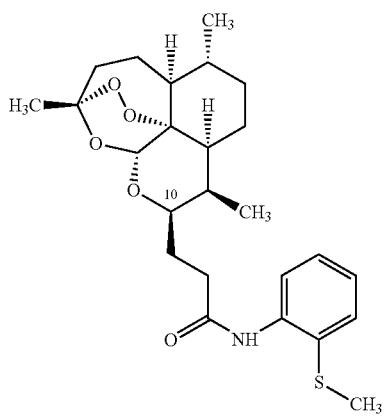

Synthesis of 2-arteSanilide 12e. To a flame dried 10 mL round bottom flask was added carboxylic acid monomer 11 (20 mg, 0.059 mmol), EDC (12.4 mg, 0.065 mmol), HOBt (8.7 mg, 0.065 mmol), and CH$_2$Cl$_2$ (1 mL). The reaction was stirred for 1 hour before commercially available 2-aminothioanisole (8.9 μL, 0.071 mmol) was added dropwise and stirred for an additional 18 hours at room temperature until TLC analysis indicated consumption of starting material. The reaction was quenched with brine (3 mL), and extracted with CH$_2$Cl$_2$ (3×3 mL). The resulting organic extracts were dried over MgSO$_4$ and concentrated in vacuo. The crude product was purified by preparative thin layer chromatography (silica gel, 40% ethyl acetate/hexanes) to afford 12e as a colorless, amorphous solid (86% yield, 23.3 mg, 0.051 mmol). FT-IR (thin film, cm$^{-1}$) 3336, 2920, 1688, 1579, 1511, 1433, 1376, 1296, 1124, 1092, 1058, 1011, 945; $^1$H-NMR (400 MHz, CDCl$_3$) δ 8.32 (bs, 1H), 7.46 (d, J=7.2 Hz, 2H), 7.27 (t, J=8.8 Hz, 1H), 7.05 (t, J=7.2 Hz, 1H), 5.34 (s, 1H), 4.16 (m, 1H), 2.75 (m, 2H), 2.51 (m, 2H), 2.37 (s, 3H), 2.32 (m, 1H), 2.08-1.79 (m, 4H), 1.69-1.57 (m, 2H), 1.52-1.21 (m, 4H), 1.38 (s, 3H), 0.95 (d, J=6.0 Hz, 3H), 0.91 (d, J=7.6 Hz, 3H); $^{13}$C NMR (100 MHz, CDCl$_3$) δ 171.5, 138.4, 132.8, 128.8, 125.3, 124.2, 120.8, 103.3, 88.8, 81.1, 75.5, 52.4, 44.4, 37.4, 36.5, 35.7, 34.5, 30.2, 26.1, 26.1, 24.9, 24.7, 20.2, 18.9, 13.1; $[α]_D^{26}$=+52.3 (c=0.63, CHCl$_3$). HRMS m/z for C$_{25}$H$_{36}$SNO$_5$(M+H) calculated 463.2392 found 463.2395.

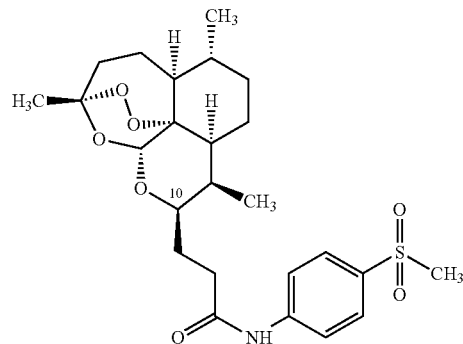

Synthesis of 4-sulfone 12i. To a stirring solution of 4-arteSanilide 12c (16.6 mg, 0.036 mmol) in CH$_2$Cl$_2$ (1 mL) was added m-CPBA (≤77%, 17.7 mg, 0.079 mmol). The reaction was stirred for 2 hours before TLC analysis indicated consumption of starting material, at which point it was quenched with saturated NaHSO$_3$ and extracted with CH$_2$Cl$_2$ (3×3 mL). The combined organic extracts were washed with saturated NaHSO$_3$ and saturated NaHCO$_3$, dried with MgSO$_4$, and concentrated under reduced pressure. The crude oil was purified by preparative thin layer chromatography (silica gel, 50% EtOAc/Hexanes) to afford 12i as a colorless, amorphous solid (91% yield, 16.2 mg, 0.033 mmol). FT-IR (thin film, cm$^{-1}$) 3691, 3371, 3745, 3317, 2939, 2361, 1668, 1608, 1542, 1493, 1454, 1428, 1376, 1285, 1211, 1152, 1090, 1088, 1054; $^1$H-NMR (300 MHz, CDCl$_3$) δ 8.12 (bs, 1H) 7.86 (d, J=6.6 Hz, 2H), 7.77 (d, J=6.6 Hz, 2H), 5.36 (s, 1H), 4.22 (dd, J=9.6, 6.6 Hz, 1H), 3.03 (s, 3H), 2.73 (q, J=4.8 Hz, 2H), 2.60 (t, J=4.8 Hz, 2H), 2.38 (td, J=10.2, 2.8 Hz, 1H), 2.07 (m, 2H), 2.35 (m, 1H), 1.94 (m, 2H), 1.81 (m, 1H), 1.63 (m, 2H), 1.41 (s, 3H), 1.28 (m, 3H), 0.96 (d, J=4.5 Hz, 3H), 0.87 (d, J=6 Hz, 3H); $^{13}$C NMR (75 MHz, CDCl$_3$) δ 172.0, 143.2, 134.8, 128.6, 122.2, 119.6, 103.5, 89.1, 81.1, 76.1, 57.3 52.2, 44.7, 44.2, 37.5, 36.4, 35.9, 34.3, 30.5, 26.0, 25.0, 24.6, 24.5, 20.4, 12.9;

$[\alpha]_D^{23}$=+43 (c=0.38, CHCl$_3$); HRMS m/z for C$_{25}$H$_{35}$SNO$_7$Na(M+Na)$^+$ calculated 516.2032 found 516.2029.

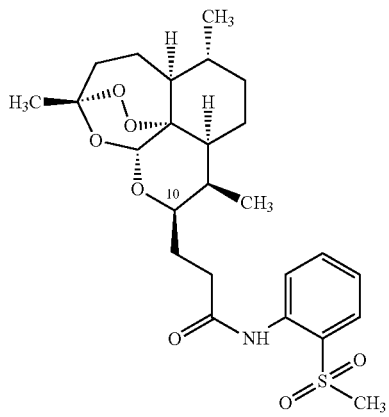

Synthesis 2-sulfone 12k. To a stirring solution of 2-arte-Sanilide 12e (3.5 mg, 0.0078 mmol) in CH$_2$Cl$_2$ (0.5 mL) was added m-CPBA (≤77%, 3.7 mg, 0.017 mmol) and stirred for 2.5 hours until TLC analysis indicated the consumption of starting material. The reaction was quenched with saturated NaHSO$_3$ and extracted with CH$_2$Cl$_2$ (3×3 mL). The combined organic extracts were washed with saturated NaHSO$_3$ and saturated NaHCO$_3$, dried with MgSO$_4$, and concentrated under reduced pressure. The crude oil was purified by preparative thin layer chromatography (silica gel, 50% EtOAc/Hexanes) to afford 12k as colorless, amorphous solid (93% yield, 3.5 mg, 0.0071 mmol). FT-IR (thin film, cm$^{-1}$) 3329, 2893, 2468, 1666, 1599, 1542, 1493, 1454, 1428, 1376, 1285, 1261, 1208, 1156, 1123, 1090, 1032, 1009; $^1$H-NMR (300 MHz, CDCl$_3$) δ 8.50 (bs, 1H), 7.85 (dd, J=7.8, 1.2 Hz, 1H), 7.61 (t, J=7.2 Hz, 1H), 7.22 (t, J=7.2, 1H), 5.32 (s, 1H), 4.15 (dd, J=9.6, 6.6 Hz, 1 H), 3.09 (m, 2H), 2.72 (m, 2H), 2.52 (m, 1H), 2.43 (s, 3H) 2.31 td, J=14.1, 3.6 1H), 2.07 (m, 2H), 2.07 (m, 2H), 1.70 (m, 3H), 1.71 (m, 4H), 1.34 (s, 3H), 0.94 (d, J=6 Hz, 3H), 0.88 (d, J=7.5 Hz, 3H). $^{13}$C NMR (75 MHz, CDCl$_3$) δ 171.6, 139.0, 135.2, 130.0, 125.5, 123.8, 122.9, 120.6, 103.3, 88.8, 82.0, 75.4, 57.8, 52.4, 44.4, 37.2, 36.7, 36.1, 35.2, 30.6, 26.4, 24.9, 24.7, 20.0, 12.9; $[\alpha]_D^{22}$=+58 (c=0.32, CHCl$_3$); HRMS m/z for C$_{25}$H$_{35}$NO$_7$SNa(M+Na) calculated 516.2032 found 516.2037.

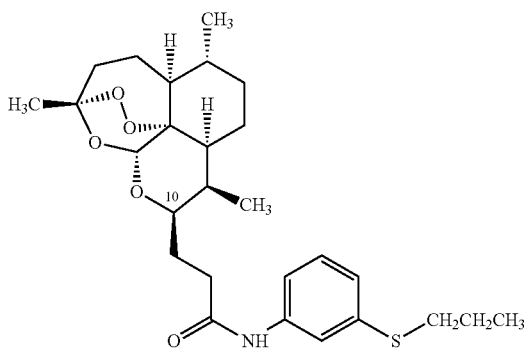

Synthesis of 3-n-Propyl Sulfide 12l. To a 10 mL round bottom flask was added carboxylic acid monomer 11 (20 mg, 0.059 mmol), EDC (12.4 mg, 0.065 mmol), HOBt (10.8 mg, 0.065 mmol), and 3-n-propylsulfanylaniline (10.8 mg, 0.065 mmol). CH$_2$Cl$_2$ (1.5 mL) was then added and the reaction was allowed to stir at room temperature for 8 hours. It was then quenched with brine, extracted with CH$_2$Cl$_2$ (3×3 mL), and dried over MgSO$_4$, and evaporated. The crude product was purified by preparative thin layer chromatography (silica gel, 30% EtOAc/Hexanes) to afford 12l as a colorless, amorphous solid (79% yield, 22.7 mg, 0.046 mmol). FT-IR (thin film, cm$^{-1}$) 3310, 2958, 2874, 1668, 1594, 1479, 1456, 1418, 1376, 1295, 1252, 1186, 1123, 1090, 1055, 1011, 876, 824, 779, 665; 1H-NMR (400 MHz, CDCl$_3$) δ 7.64 (bs, 1H), 7.56 (s, 1H), 7.28 (d, J=8.0 Hz, 1H), 7.17 (t, J=8.0 Hz, 1H), 7.01 (d, J=8.0 Hz, 1H), 5.32 (s, 1H), 4.17 (m, 1H), 2.88 (t, 7.2 Hz, 2H), 2.72 (m, 1H), 2.62-2.43 (m, 2H), 2.32 (m, 1H), 2.03-1.77 (m, 5H), 1.70-1.53 (m, 3H), 1.65 (sex, J=7.2 Hz, 2H), 1.48-1.20 (m, 4H), 1.37 (s, 3H), 1.00 (t, J=7.2 Hz, 3H), 0.92 (d, J=8.8 Hz, 3H), 0.87 (J=10.4 Hz, 3H); $^{13}$C-NMR (100 MHz, CDCl$_3$) 171.3, 138.6, 137.9, 129.1, 124.2, 119.6, 117.0 103.4, 89.0, 81.1, 75.8, 52.3, 44.3, 37.4, 36.5, 36.1, 35.4, 34.4, 30.2, 26.1, 25.1, 24.9, 24.7, 22.4, 20.2, 13.4, 13.0; $[\alpha]_D^{26}$=+36.4 (c=0.40, CHCl$_3$); ESI-HRMS m/z for C$_{27}$H$_{40}$NO$_5$S(M+H)$^+$ calc. 490.2633, found 490.2640.

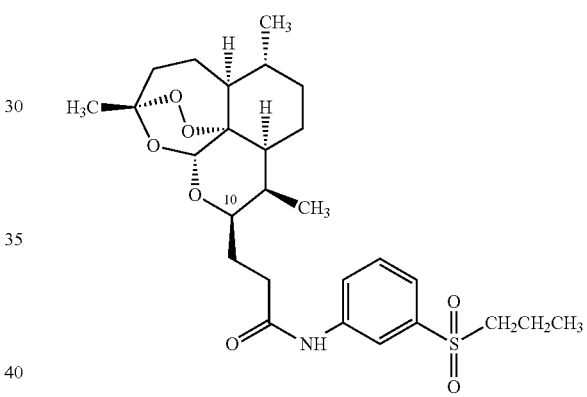

Synthesis of 3-n-Propyl Sulfone 12m. To a stirring solution of 3-n-propyl sulfide 12l (10 mg, 0.020 mmol) in CH$_2$Cl$_2$ (1 mL) was added m-CPBA (≤77%, 7.8 mg, 0.045 mmol). The solution was allowed to stir for 3 hours before it was quenched with saturated NaHSO$_3$ (3 mL) and extracted with CH$_2$Cl$_2$ (3×4 mL). The combined organic extracts were washed with saturated NaHSO$_3$ and saturated NaHCO$_3$, dried with MgSO$_4$, and concentrated under reduced pressure. The crude oil was purified by preparative thin layer chromatography (silica gel, 45% EtOAc/Hexanes) to afford 12m as a colorless, amorphous solid (10.3 mg, 0.020 mmol, 97% yield). FT-IR (thin film, cm$^{-1}$) 3333, 2926, 2363, 1697, 595, 1540, 1478, 1420, 1376, 1302, 1250, 1139, 1091, 1054, 1010, 876, 757; $^1$H-NMR (400 MHz, CDCl$_3$) δ 8.20 (bs, 1H), 8.04 (m, 1H), 7.97 (d, J=8.4 Hz, 1H), 7.60 (d, J=7.6 Hz, 1H), 7.49 (t, J=8.0 Hz, 1H), 5.36 (s, 1H), 4.21 (m, 1H), 3.08 (m, 2H), 2.75 (m, 1H), 2.67-2.52 (m, 2H), 2.34 (m, 1H), 2.06-1.79 (m, 5H), 1.75-1.62 (m, 4H), 1.49-1.19 (m, 5H), 1.31 (s, 3H), 0.99 (t, J=7.2 Hz, 3H), 0.94 (d, J=6.8 Hz, 3H), 0.91 (J=7.6 Hz, 3H); $^{13}$C-NMR (100 MHz, CDCl$_3$) δ 171.8, 139.7, 139.3, 129.8, 124.8, 123.0, 119.0, 103.5, 89.0, 81.1, 57.8, 52.3, 44.3, 37.4, 36.5, 36.1, 34.4, 30.2, 29.7, 26.0, 25.0, 24.9, 24.7, 20.1, 16.5, 13.0, 12.9; $[\alpha]_D^{27}$=+25.7 (c=0.59, CHCl$_3$); ESI-HRMS m/z for C$_{27}$H$_{40}$NO$_7$S(M+H)$^+$ calc. 522.2523, found 522.2524.

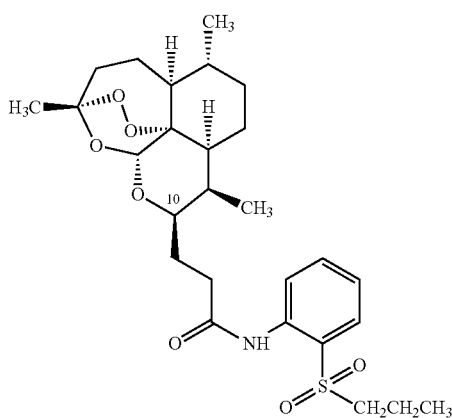

Synthesis of 2-n-propyl sulfone 12n. To a 10 mL round bottom flask was added carboxylic acid monomer 11 (11.7 mg, 0.035 mmol), EDC (7.8 mg, 0.042 mmol), HOBt (1 mg, 6.9 μmol), and 2-n-propylsulfenylaniline (6.9 mg, 0.042 mmol). CH$_2$Cl$_2$ (1 mL) was then added and the reaction was allowed to stir at room temperature for 20 hours. It was then quenched with brine (3 mL), extracted with CH$_2$Cl$_2$ (3×3 mL), dried over MgSO$_4$, and evaporated. The crude product was dissolved in CH2Cl2 (1 mL) and m-CPBA (≤77%, 16.9 mg, 0.076 mmol) was added. The resulting solution was allowed to stir for 1.5 hours before the reaction was quenched with NaHSO$_3$ (2 mL) and extracted with CH$_2$Cl$_2$ (3×4 mL). The combined organic extracts were washed with NaHSO$_3$ and NaHCO$_3$, dried with MgSO$_4$, and evaporated. The resulting crude oil was purified by preparative thin layer chromatography (silica gel, 50% EtOAc/Hexanes) to afford 12l as a colorless, amorphous solid (57% yield over 2 steps, 10.2 mg, 0.020 mmol). FT-IR (thin film, cm$^{-1}$) 3345, 2931, 2349, 1688, 1601, 1539, 1476, 1428, 1391, 1266, 1212, 1061, 1012; 1H-NMR (300 MHz, CDCl$_3$) δ 9.60 (bs, 1H), 8.50 (d, J=8.4 Hz, 1H), 7.85 (dd, J=10.4, 1.6 Hz, 1H), 7.61 (t, J=7.2 Hz, 1H), 7.22 (t, J=7.2 Hz, 1H), 5.32 (s, 1H), 4.15 (m, 1H), 3.09 (m, 2H), 2.72 (m, 2H), 2.52 (m, 1H), 2.31 (m, 1H), 2.13-1.56 (m, 5H), 1.73 (t, J=7.8 Hz, 2H), 1.72-1.62 (m, 4H), 1.46-1.18 (m, 3H), 1.35 (s, 3H), 1.00 (t, J=7.5 Hz, 3H), 0.95 (d, J=6.0 Hz, 3H), 0.91 (J=8.5 Hz, 3H); $^{13}$C-NMR (75 MHz, CDCl$_3$) δ 171.6, 137.5, 135.2, 130.0, 125.5, 123.8, 122.9, 103.3, 88.8, 81.1, 75.4, 57.8, 52.4, 44.4, 37.4, 36.5, 36.1, 34.4, 30.2, 26.1, 25.5, 24.7, 24.6, 20.2, 16.2, 13.1, 12.9; [α]$_D^{27}$=+25.7 (c=0.59, CHCl$_3$); ESI-HRMS m/z for C$_{27}$H$_{40}$NO$_7$S(M+H)$^+$ calculated 522.2525, found 522.2521.

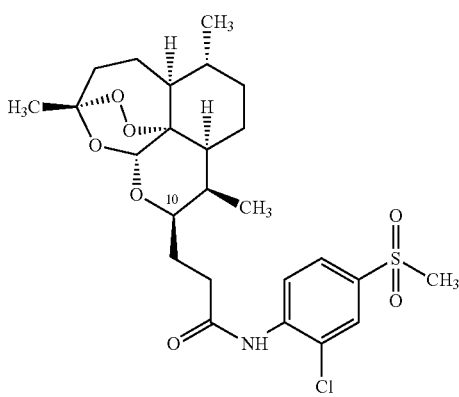

Synthesis of 2-chloro-4-sulfone 12o. To a flame dried 10 mL round bottom flask charged with carboxylic acid monomer 11 (33.5 mg, 0.098 mmol) and N-methylmorpholine (12 μL, 0.108 mmol) in anhydrous THF (1 mL) was added isobutyl chloroformate (13 μL, 0.108 mmol) at −40° C. The solution was stirred for 1 hour. Meanwhile, in a flame dried 10 mL pear shaped flask, nBuli (1.4 M in toluene, 0.41 mL, 0.57 mmol) was added to a solution of commercially available 2,4-bis(methylsulfonyl)aniline (121.5 mg, 0.59 mmol) in THF (2 mL) at −78° C. The solution was stirred for 20 minutes before it was warmed to 0° C., at which point it was stirred for an additional 10 minutes. This anilide solution was then pre-cooled to −40° C. and slowly added to former reaction via cannula. The reaction was stirred for 5 hours at −40° C. before it was quenched with saturated NH$_4$Cl (5 mL).

The mixture was extracted with EtOAc (3×4 mL), washed with brine, and purified by thin layer chromatography (45% EtOAc/Hexanes) to afford 12o as a colorless amorphous solid (37% yield, 19.2 mg, 0.036 mmol). FT-IR (thin film, cm$^{-1}$) 3328, 2931, 1672, 1598, 1538, 1463, 1439, 1376, 1311, 1239, 1141, 1058, 1008, 878. 1H-NMR (400 MHz, CDCl$_3$) δ 8.58 (bs, 1H), 7.83 (d, J=6.6 Hz, 1H), 7.59 (s, 1H), 7.22 (dd, J=7.1, 2.2 Hz, 1H), 5.31 (s, 1H), 4.15 (m, 1H), 3.09 (m, 2H), 2.72 (m, 1H), 2.31 (m, 2H), 2.63 (s, 3H), 2.35 (m, 3H), 2.03-1.66 (m, 4H), 1.40 (s, 3H) 1.39-1.17 (m, 4H), 0.93 (d, J=7.2 Hz, 3H), 0.89 (d, J=6.8 Hz, 3H); $^{13}$C NMR (100 MHz, CDCl$_3$) δ 171.4, 136.6, 134.8, 134.3, 130.1, 128.9, 122.1, 118.9, 112.2, 69.6, 56.8, 56.4, 53.6, 47.2, 46.4, 41.1, 39.4, 36.2, 35.1, 33.6, 27.9, 24.1, 22.8, 19.8, 12.8; [α]$_D$23=+33 (c=0.56, CHCl$_3$); HRMS m/z calculated for C$_{25}$H$_{34}$ClNO$_7$S(M+H) 528.1823, found 528.1828.

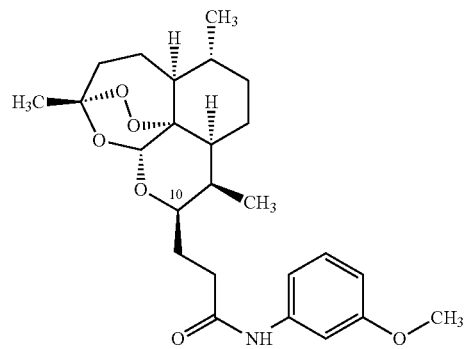

Synthesis of 3-methyl ether 12p. To a flame dried 10 mL round bottom flask was added carboxylic acid monomer 11 (25 mg, 0.073 mmol), EDC (15.4 mg, 0.081 mmol), HOBt (10.9 mg, 0.081 mmol), and CH$_2$Cl$_2$ (1 mL). The reaction was stirred for 1 hour before commercially available m-anisidine (9.2 μL, 0.081 mmol) was added dropwise and stirred for an additional 5 hours at room temperature until TLC analysis indicated consumption of starting material. The reaction was quenched with brine (3 mL), and extracted with CH$_2$Cl$_2$ (3×3 mL). The resulting organic extracts were dried over MgSO$_4$ and concentrated in vacuo. The crude product was purified by preparative thin layer chromatography (silica gel, 40% ethyl acetate/hexanes) to afford 12p as a colorless, amorphous solid (92% yield, 29.9 mg, 0.067 mmol). FT-IR (thin film, cm$^{-1}$) 3317, 2939, 1668, 1608, 1542, 1493, 1454, 1428, 1376, 1285, 1261, 1208, 1156, 1123, 1090, 1053, 1011; 1H-NMR (400 MHz, CDCl$_3$) δ 7.75 (bs, 1H), 7.34 (s, 1H), 7.18 (t, J=8.0 Hz, 1H), 7.00 (d, J=7.6 Hz, 1H), 6.63 (dd, J=8.0, 2.0 Hz, 1H), 5.35 (s, 1H), 4.16 (m, 1H), 3.79 (s, 3H), 2.76-2.60 (m, 2H), 2.47 (m, 1H), 2.33 (m, 1H), 2.04-1.78 (m, 6H), 1.67-1.53 (2H), 1.49-1.18 (4H), 1.38 (s, 3H), 0.94 (d, J=10.8 Hz, 3H), 0.89 (J=7.6 Hz, 3H); $^{13}$C NMR (100 MHz, CDCl$_3$) δ 171.6, 160.3, 139.6, 129.7, 11.9, 110.0, 105.4, 103.7, 89.1, 81.3, 75.9, 55.4, 52.6, 44.6, 37.5, 36.6, 35.9, 34.4, 30.3, 36.1, 25.0, 24.9, 24.7, 20.2, 13.0; $[\alpha]_D 25=+45.6$ (c=1.36, CHCl$_3$); ESI-HRMS m/z for C$_{25}$H$_{36}$NO$_6$(M+H)$^+$ calc. 446.2549, found 446.2546.

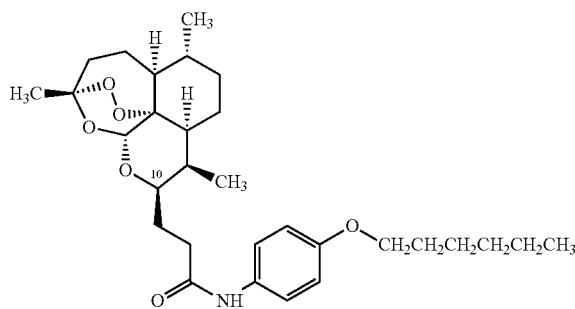

Synthesis of 4-hexyl ether 12q. To a flame dried 10 mL round bottom flask was added carboxylic acid monomer 11 (20 mg, 0.059 mmol, 1.0 eq), EDC (11 mg, 0.07 mmol, 1.2), HOBt (9.5 mg, 0.07 mmol, 1.2 eq), and CH$_2$Cl$_2$ (1 mL). The reaction was stirred for 1 hour before commercially available 4-(hexyloxy)aniline (13.5 mg, 0.07 mmol, 1.2 eq) was added dropwise and stirred for an additional 5 hours at room temperature until TLC analysis indicated consumption of starting material. The reaction was quenched with brine (3 mL), and extracted with CH$_2$Cl$_2$ (3×3 mL). The resulting organic extracts were dried over MgSO$_4$ and concentrated in vacuo. The crude product was purified by preparative thin layer chromatography (silica gel, 40% ethyl acetate/hexanes) to afford 12q as a colorless, amorphous solid (60% yield, 18.0 mg, 0.035 mmol). FT-IR (cm$^{-1}$) 3308, 2935, 2871, 1658, 1603, 1542, 1510, 1453, 1412, 1377, 1240, 1173, 1124, 1090, 1056, 1011, 937, 876, 828, 754; $^1$H NMR (400 MHz, CDCl$_3$) δ 7.64 (s, 1 H), 7.41 (d, J=8.91 Hz, 2 H), 6.82 (d, J=8.91 Hz, 2 H), 5.34 (s, 1 H), 4.15 (ddd, J=11.01, 6.02, 1.86 Hz, 1 H), 3.91 (t, J=6.57 Hz, 2 H), 2.79-2.70 (m, 1 H), 2.64-2.55 (m, 1 H), 2.50-2.40 (m, 1 H), 2.33 (td, J=13.91, 3.69 Hz, 1 H), 2.05-1.95 (m, 2 H), 1.94-1.86 (m, 2 H), 1.84-1.71 (m, 3 H), 1.67-1.55 (m, 2 H), 1.46-1.41 (m, 3 H), 1.38 (s, 4 H), 1.36-1.29 (m, 5 H), 1.28-1.22 (m, 2 H), 0.95 (d, J=5.87 Hz, 4 H), 0.89 (t, J=6.76 Hz, 5 H); $^{13}$C NMR (100 MHz, CDCl$_3$) δ 171.1, 155.8, 131.1, 121.7, 114.7, 103.5, 88.9, 81.2, 76.1, 68.3, 52.4, 44.4, 37.4, 36.5, 35.7, 34.4, 31.6, 30.2, 29.3, 26.1, 25.7, 25.0, 24.9, 24.7, 22.6, 20.2, 14.1, 13.2; $[\alpha]_D^{25}$ +43.78 (c=0.1.245, CHCl$_3$); ESI-HRMS m/z (M+H)$^+$ for C$_{30}$H$_{46}$NO$_6$ calc. 516.3331, found=516.3326.

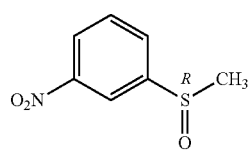

Synthesis of sulfoxide (+)-(R)-14. Commercially available racemic sulfide 13 (500 mg, 2.96 mmol) was dissolved in HOAc:MeOH (1:3, 6 mL), and H$_2$O$_2$ (30% in H$_2$O, 2 mL) was added at room temperature. The reaction was allowed to stir for 24 hours before it was quenched with saturated NaHCO$_3$ (8 mL) at 0° C., and extracted with CH$_2$Cl$_2$ (3×5 mL). The combined organic layers were dried with MgSO$_4$ and concentrated in vacuo. The resulting solid was purified by column chromatography (silica gel, 20-40% EtOAc/Hexanes) to afford racemic sulfoxide 14 as a colorless solid (91% yield, 499.0 mg, 2.69 mmol). Sulfoxide (+)-(R)-14 was resolved by chiral HPLC (Regis Whelk-01 (S,S); 20% IPA in hexanes; detection wavelength 254 nm; flow rate=2.5 mL/min) tr=82.0 min (R)-enantiomer and 95.7 min (S)-enantiomer. Spectral and physical properties match that which has been reported in the literature. Tohma, H., et al., Hypervalent Iodine(V)-Induced Asymmetric Oxidation of Sulfides to Sulfoxides Mediated by Reversed Micelles: Novel Nonmetallic Catalytic System, J. Org. Chem. 1999, 64, 3519-3523. $[\alpha]_D^{22.4}$=+123.7 (CHCl$_3$, 0.80).

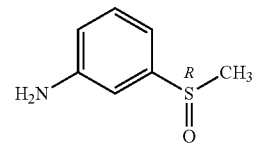

Synthesis of sulfenyl aniline (+)-(R)-15. To a suspension of Raney nickel (catalytic) and (+)-(R)-14 (20 mg, 0.11 mmol) in MeOH (1 mL) was added hydrazine (0.5 mL). The reaction was stirred for 18 hours before it was filtered through celite and washed with MeOH (3×5 mL). The filtrate was diluted with saturated NH$_4$Cl (10 mL) and extracted with EtOAc (3×5 mL). The combined organic layers were washed with saturated NH$_4$Cl and brine, dried with MgSO$_4$, and concentrated under reduced pressure. Crude sulfoxide (+)-(R)-15 was purified by column chromatography (silica gel, 1-10% MeOH/CH$_2$Cl$_2$) to afford (+)-(R)-15 as a colorless solid (81% yield, 13.5 mg, 0.087 mmol). Spectral and physical properties match that which has been reported in the literature. Folli, U., et al., Intramolecular hydrogen bonds in aromatic suphoxides: $^1$H nuclear magnetic resonance and acidity constant measurements. J. Chem. Soc. Perkin Trans. 2, 1973, 848-853. $[\alpha]_D^{23}$=+177.2 (CHCl$_3$, c=0.11).

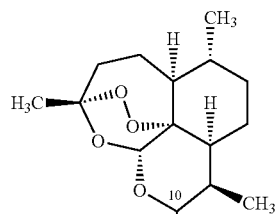

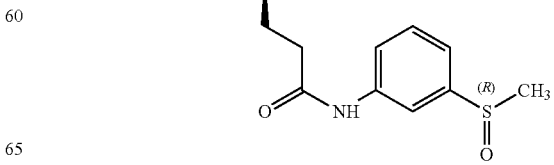

Synthesis of 3-(R)-sulfoxide 12h. Carboxylic acid 5 (15 mg, 0.043 mmol), EDC (10.0 mg, 0.052 mmol), and HOBt (7.1 mg, 0.052 mmol) were dissolved in $CH_2Cl_2$ (2 mL) in a 10 mL round bottom flask. The solution was stirred for 15 minutes at room temperature before (+)-15 (8.1 mg, 0.052 mmol) was added. The reaction was allowed to stir for 36 hours before it was quenched with brine (3 mL) and extracted with $CH_2Cl_2$ (3×4 mL). The combined organic layers were dried with $MgSO_4$ and concentrated under reduced pressure. The resulting crude oil was purified by preparative thin layer chromatography (silica gel, 100% EtOAc) to afford sulfoxide diastereomer 12h (48% yield, mg, 10.1 mg, 0.021 mmol).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Olliaro, P. L.; Boland, P. B. Clinical Public Health Implications of Antimalarial Drug Resistance. In Antimalarial Chemotherapy: Mechanisms of Action, Resistance, and New Directions in Drug Discovery; Rosenthal, P. J., Ed.; Humana Press: Totowa, N.J., 2001; pp. 65-83.

Guidelines for the Treatment of Malaria; World Health Organization: Geneva, 2006.

Ashley, E. A.; White, N. J. Artemisinin-based Combinations. Curr. Opin. Infect. Dis. 2005, 18, 531-536.

Adjuik, M.; Babiker, A.; Garner, P.; Olliaro, P.; Taylor, W.; White, N. Artesunate Combinations for Treatment of Malaria: Meta-analysis. Lancet 2004, 363, 9-17.

Guthmann, J.-P.; Cohuet, S.; Rigutto, C.; Fortes, F.; Saraiva, N.; Kiguli, J.; Kyomuhendo, J.; Francis, M.; Noel, F.; Mulemba, M. Balkan, S. High Efficacy of Two Artemisinin-based Combinations (Artesunate plus Amodiaquine and Artemether plus Lumefantrine) in Caala, Central Angola. Am. J. Trop. Med. Hyg. 2006, 75, 143-145.

Myint, H. Y.; Ashley, E. A.; Day, N. P. J.; Nosten, F.; White, N. J. Efficacy and Safety of Dihydroartemisinin-piperaquine. Trans. R. Soc. Trop. Med. Hyg. 2007, 101, 858-866.

Sirima, S. B.; Tiono, A. B.; Gansane, A.; Diana, A.; Ouedraogo, A.; Konate, A. T.; Kiechel, J. R.; Morgan, C. C.; Olliaro, P. L.; Taylor, W. R. J., The Efficacy and Safety of a New Fixed-dose Combination of Amodiaquine and Artesunate in Young African Children with Acute Uncomplicated Plasmodium falciparum. Malar. J. 2009, 8, 48.

De Pilla Varotti, F.; Botelho, A. C. C.; Andrade, A. A.; de Paula, R. C.; Fagundes, E. M. S.; Valverde, A.; Mayer, L. M. U.; Mendonca, J. S.; de Souza, M. V. N.; Boechat, N.; Krettli, A. U. Synthesis, Antimalarial Activity, and Intracellular Targets of MEFAS, a New Hybrid Compound Derived from Mefloquine and Artesunate. Antimicrob. Agents Chemother. 2008, 52, 3868-3874.

Sagara, I.; Diallo, A. D.; Kone, M.; Coulibaly, M.; Diawara, S. I.; Guindo, O.; Maiga, H.; Niambele, M. B.; Sissoko, M.; Dicko, A.; Djimde, A.; Doumbo, O. K. A Randomized Trial of Artesunate-mefloquine versus Artemether-lumefantrine for Treatment of Uncomplicated Plasmodium falciparum Malaria in Mali. Am. J. Trop. Med. Hyg. 2008, 79, 655-661.

Bhatt, K. M.; Samia, B. M.; Bhatt, S. M.; Wasunna, K. M. Efficacy and Safety of an Artesunate/mefloquine Combination, (Artequin) in the Treatment of Uncomplicated P. falciparum Malaria in Kenya. East Afr. Med. J. 2006, 83, 236-242.

Charman, S. A.; Arbe-Barnes, S.; Bathurst, I. C.; Brun, R.; Campbell, M.; Charman, W. N.; Chiu, F. C. K.; Chollet, J.; Craft, J. C.; Creek, D. J.; Dong, Y.; Matile, H.; Maurer, M.; Morizzi, J.; Nguyen, T.; Papastogiannidis, P.; Scheurer, C.; Shackleford, D. M.; Sriraghavan, K.; Stingelin, L.; Tang, Y.; Urwyler, H.; Wang, X.; White, K. L.; Wittlin, S.; Zhou, L.; Vennerstrom, J. L. Synthetic Ozonide Drug Candidate OZ439 Offers New Hope for a Single-dose Cure of Uncomplicated Malaria. PNAS, 2011, 108, 4400-4405.

Rosenthal, A. S.; Chen, X.; Liu, J. O.; West, D. C.; Hergenrother, P. J.; Shapiro, T. A.; Posner, G. H. Malaria-infected Mice are Cured by a Single Oral Dose of New Dimeric Trioxane Sulfones Which are Also Selectively and Powerfully Cytotoxic to Cancer Cells. J. Med. Chem. 2009, 52, 1198-1203.

Moon, D. K.; Tripathi, A.; Sullivan, D.; Siegler, M. A.; Parkin, S.; Posner, G. H. A Single, Low, Oral Dose of a 5-Carbon-linked Trioxane Dimer Orthoester Plus Mefloquine Cures Malaria-infected Mice. Bioorg. Med. Chem. Lett. 2011, 21, 2773-2775.

Woodard, L. E.; Chang, W.; Chen, X.; Liu, J. O.; Shapiro, T. A.; Posner, G. H. Malaria-Infected Mice Live Until at Least Day 30 After a New Monomeric Trioxane Combined with Mefloquine are Administered Together in a Single Low Oral Dose. J. Med. Chem. 2009, 52, 7458-7462.

Posner, G. H.; Paik, I.-H.; Sur, S.; McRiner, A. J.; Borstnik, K.; Xie, S.; Shapiro, T. A. Orally Active, Antimalarial, Anticancer, Artemisinin-derived Trioxane Dimers with High Stability and Efficacy. J. Med. Chem. 2003, 46, 1060-1065.

Haynes, R. K.; Fugmann, B.; Stetter, J.; Rieckmann, K.; Heilmann, H-D.; Chan, H-W.; Cheung, M-K.; Lam, W-L.; Wong, H-N.; Croft, S. L.; Vivas, L.; Rattray, L.; Stewart, L.; Peters, W.; Robinson, B. L.; Edstein, M. D.; Kotecka, B.; Kyle, D. E.; Beckermann, B.; Gerisch, M.; Radtke, M.; Schmuck, G.; Steinke, W.; Wollborn, U.; Schmeer, K.; Römer, A. Artemisone—A Highly Active Antimalarial Drug of the Artemisinin Class. Angew. Chem. Int. Ed. 2006, 45, 2082-2088.

Posner, G. H.; O'Dowd, H.; Caferro, T.; Cumming, J. N.; Ploypradith, P.; Xie, S.; Shapiro, T. A. Antimalarial Synthetic Sulfone Trioxanes. Tetrahedron Lett. 1998, 39, 2273-2276.

Bachi, M. D.; Korshin, E. E.; Hoos, R.; Szpilman, A. M.; Ploypradith, P.; Xie, S.; Shapiro, T. A.; Posner, G. H. A Short Synthesis and Biological Evaluation of Potent and Nontoxic Antimalarial Bridged Bicyclic β-Sulfonyl-Endoperoxides. J. Med. Chem. 2003, 46, 2516-2533.

Amewu, R.; Gibbon, P.; Mukhtar, A.; Stachulski, A. V.; Ward, S. A.; Hall, C.; Rimmer, K.; Davies, J.; Vivas, L.; Bacsa, J.; Mercer, A. E.; Nixon, G.; Stocks, P. A.; O'Neill, P. M. Synthesis, in vitro and in vivo Antimalarial Assessment of Sulfide, Sulfone and Vinyl Amide-substituted 1,2, 4-Trioxanes Prepared via Thiol-olefin Co-oxygenation (TOCO) of Allylic Alcohols. *Org. Biomol. Chem.* 2010, 8, 2068-2077.

Jung, M.; Tak, J.; Chung, W-Y.; Park, K-K. Antiangiogenic Activity of Deoxoartemisinin Derivatives on Chorioallantoic Membrane. *Bioorg. Med. Chem. Lett.* 2006, 16, 1227-1230.

Tenter, A. M., A. R. Heckeroth, and L. M. Weiss. 2000. *Toxoplasma gondii*: from animals to humans. Intl. J. Parasitol. 30:1217-1258.

Bachmann, S., J. Schroder, C. Bottmer, E. F., Torrey, and R. H. Yolken. 2005. Psychopathology in first-episode schizophrenia and antibodies to *Toxoplasma gondii*. Psychopathol. 38(2):87-90.

Berens, R. L., E. C. Krug, P. B. Nash, and T. J. Curiel. 1998. Selection and characterization of *Toxoplasma gondii* mutants resistant to artemisinin J Infect. Dis. 177:1128-1131.

Georgiev, V. S. 1994. Management of toxoplasmosis. Drugs. 48(2):179-188.

Chang, H. R., C. W. Jefford, and J.-C. Pechere. 1989. In vitro effects of three new 1,2,4-trioxanes (pentatroxane, thiahexatroxane, and hexatroxanone) on *Toxoplasma gondii*. Antimicrob. Agents Chemother. 33(10): 1748-1752.

Holfels, E., J. McAuley, D. Mack, W. K. Milhous, and R. McLeod. 1994. In vitro effects of artemisinin ether, cycloguanil hydrochloride (alone and in combination with sulfadiazine), quinine sulfate, mefloquine, primaquine phosphate, trifluoperazine hydrochloride, and verapamil on *Toxoplasma gondii*. Antimicrob. Agents Chemother. 38(6):1392-1396.

Ou-Yang, K., E. C. Krug, J. J. Man, and R. L. Berens. 1990 Inhibition of growth of *Toxoplasma gondii* by Qinghaosu and derivatives. Antimicrob. Agents Chemother. 34(10):1961-1965.

Lin A. J., D. L. Klayman, and W. K. Milhous. 1987. Antimalarial activity of new water-soluble dihydroartemisinin derivatives. J. Med. Chem. 30:2147-2150.

O'Neill P. M., Posner G. H. A medicinal chemistry perspective on artemisinin and related endoperoxides. J. Med. Chem. 2004, 47, 2945-2964.

Torrey E F, Bartko J J, Lun Z R, Yolken R H. 2007. Antibodies to *Toxoplasma gondii* in patients with schizophrenia: a meta-analysis. Schizophr. Bull. 33(3):729-736.

Jones-Brando, L., E. F. Torrey, and R. Yolken. 2003. Drugs used in the treatment of schizophrenia and bipolar disorder inhibit the replication of *Toxoplasma gondii*. Schizophr. Res. 62:237-244.

Tohma, H., et al., Hypervalent Iodine(V)-Induced Asymmetric Oxidation of Sulfides to Sulfoxides Mediated by Reversed Micelles: Novel Nonmetallic Catalytic System, *J. Org. Chem.* 1999, 64, 3519-3523.

Menan, H., et al., Comparative Study of the Efficacy and Tolerability of Dihydroartemisinin-Piperaquine-Trimethoprim versus Artemether-Lumefantrine in the Treatment of Uncomplicated *Plasmodium falciparum* Malaria in Cameroon, Ivory Coast and Senegal, *Malar. J.* 2011, 10, 185-193.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

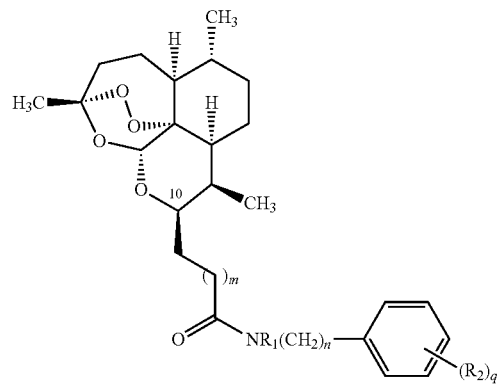

wherein:

m is an integer selected from the group consisting of 0, 1, 2, and 3;

n is an integer selected from the group consisting of 0, 1, 2, 3, and 4;

q is an integer selected from the group consisting of 1, 2, 3, 4, and 5;

$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

each occurrence of $R_2$ is independently selected from the group consisting of hydroxyl, mercapto, nitro, halogen, unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl, —$SR_3$, —$S(O_2)R_3$, —$S(O)R_3$, wherein $R_3$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

provided that if one occurrence of $R_2$ is halogen, then at least one occurrence of $R_2$ must be —$SR_3$, —$S(O_2)R_3$, —$S(O)R_3$;

or an enantiomer, diastereomer, racemate or pharmaceutically acceptable salt, prodrug, or solvate thereof.

2. The compound of claim 1, wherein the compound of Formula (I) is selected from the group consisting of:

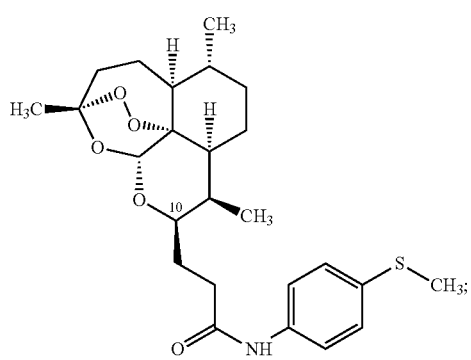
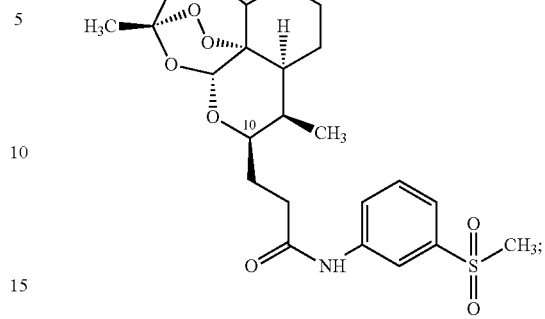
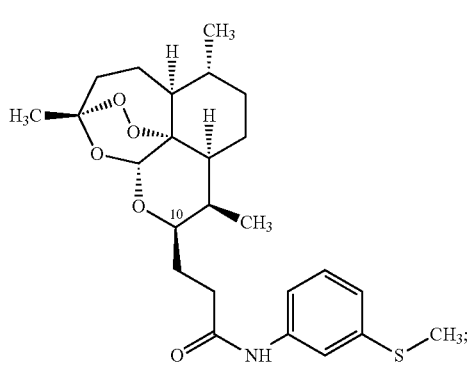
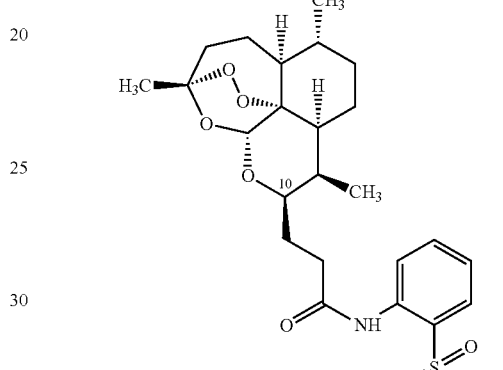
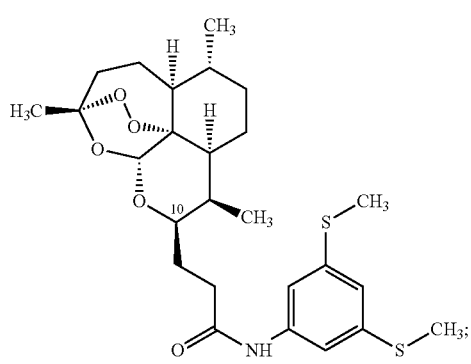
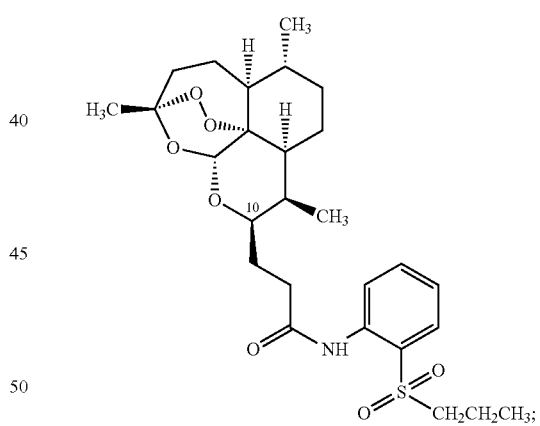
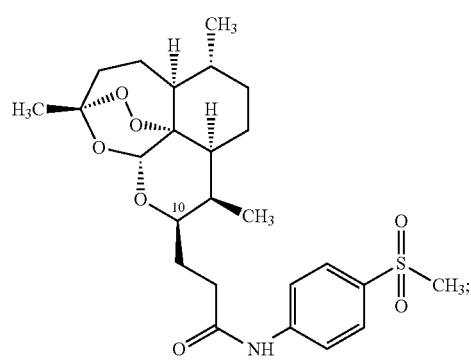
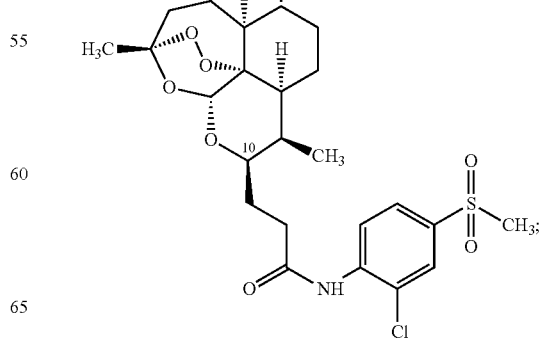

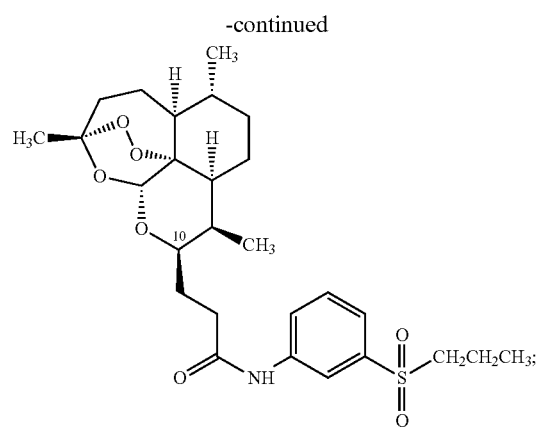
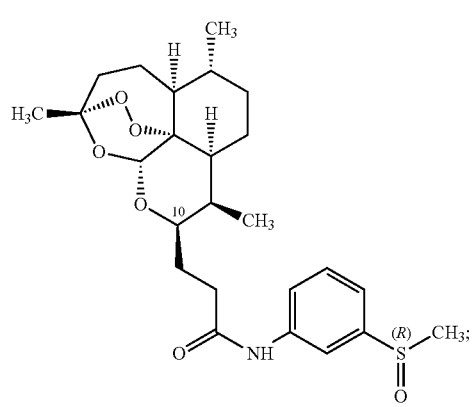
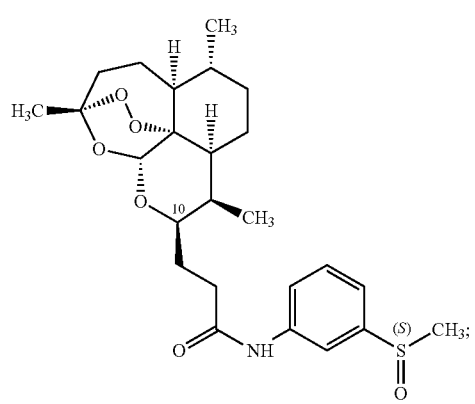
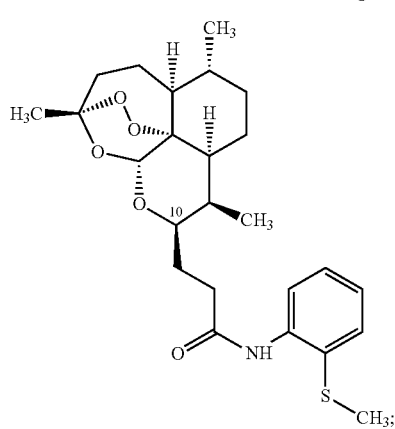
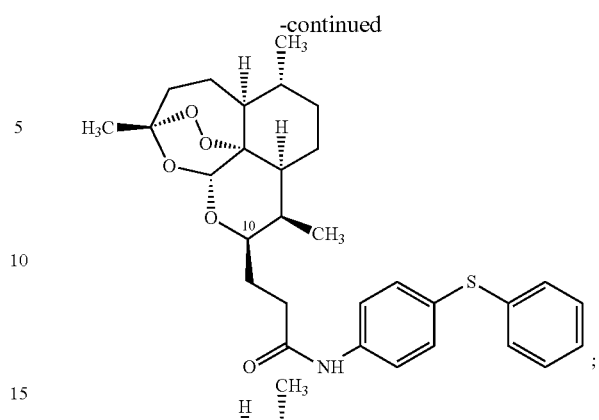
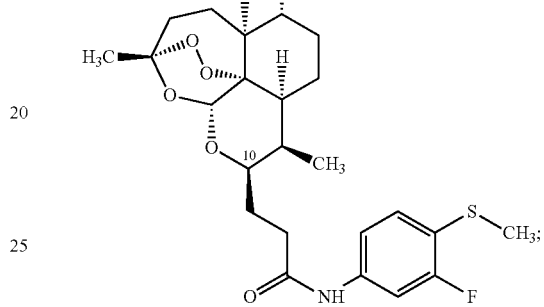
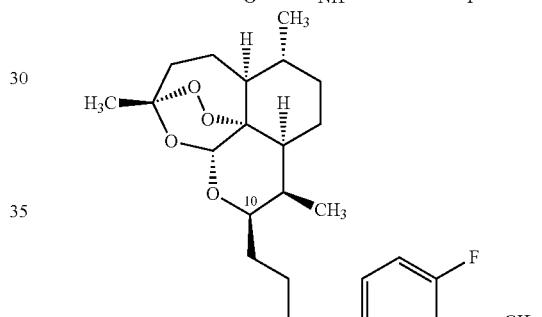
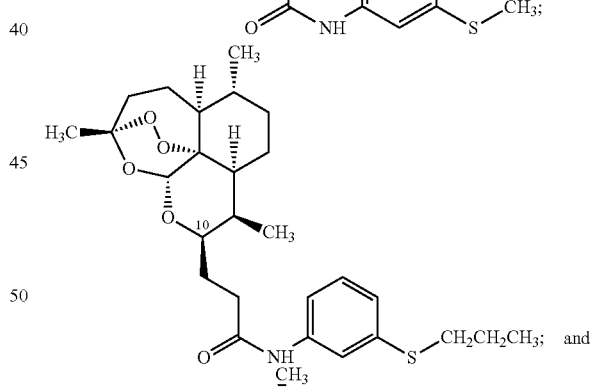
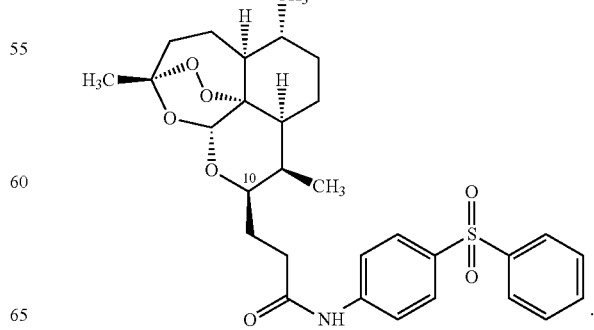

3. A pharmaceutical composition comprising a compound of formula (I) of claim 1.

4. A method for preventing, controlling or treating a plasmodia parasite infection in a subject in need of such treatment, comprising administering to the subject a therapeutically-effective amount of a compound of formula (I):

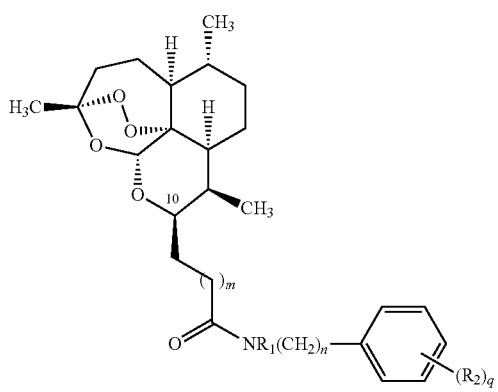

wherein:
m is an integer selected from the group consisting of 0, 1, 2, and 3;
n is an integer selected from the group consisting of 0, 1, 2, 3, and 4;
q is an integer selected from the group consisting of 1, 2, 3, 4, and 5;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
each occurrence of $R_2$ is independently selected from the group consisting of hydroxyl, mercapto, nitro, halogen, unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl, —$SR_3$, —$S(O_2)R_3$, —$S(O)R_3$, wherein $R_3$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
provided that if one occurrence of $R_2$ is halogen, then at least one occurrence of $R_2$ must be —$SR_3$, —$S(O_2)R_3$, —$S(O)R_3$;
or an enantiomer, diastereomer, racemate or pharmaceutically acceptable salt, prodrug, or solvate thereof.

5. The method of claim 4, wherein the plasmodia parasite infection is selected from the group consisting of Plasmodium falciparum, Plasmodium vivax, and Plasmodium berghei.

6. The method of claim 4, further comprising administering to the subject a quinoline anti-malarial drug concurrently or sequentially with the compound of formula (I).

7. The method of claim 6, wherein the quinoline anti-malarial drug is selected from the group consisting of chloroquine, quinine, mefloquine, and primaquine, or a pharmaceutically acceptable salt thereof.

8. A compound selected from the group consisting of:

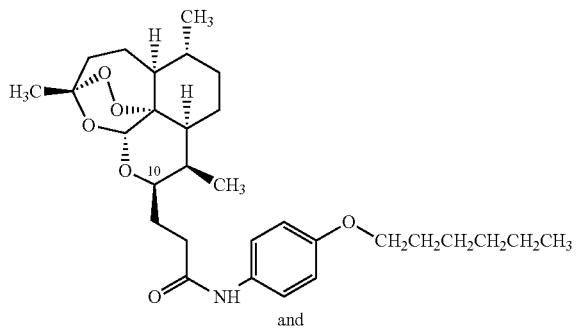

and

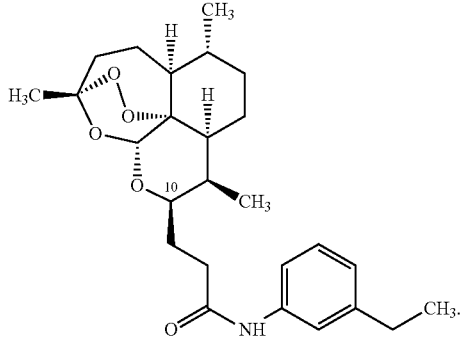

9. A method for preventing, controlling or treating a plasmodia parasite infection in a subject in need of such treatment, comprising administering to the subject a therapeutically-effective amount of a compound of claim 8.

* * * * *

UNITED STATES PATENT AND TRADEMARK OFFICE
CERTIFICATE OF CORRECTION

PATENT NO. : 9,493,480 B2  
APPLICATION NO. : 14/111991  
DATED : November 15, 2016  
INVENTOR(S) : Gary H. Posner and Rachel D. Slack Page 1 of 1

It is certified that error appears in the above-identified patent and that said Letters Patent is hereby corrected as shown below:

In the Specification

Column 1, Line 15, Replace the second paragraph as follows:  
STATEMENT OF GOVERNMENTAL INTEREST  
This invention was made with government support under AI034885, awarded by the National Institutes of Health. The government has certain rights in the invention.

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*